United States Patent
Al-Jumaily et al.

(10) Patent No.: US 11,896,770 B2
(45) Date of Patent: Feb. 13, 2024

(54) FABRIC AND METHOD OF MANUFACTURING

(71) Applicant: AUT Ventures Limited, Auckland (NZ)

(72) Inventors: Ahmed Al-Jumaily, Auckland (NZ); Sandra Grau Bartual, Auckland (NZ)

(73) Assignee: AUT Ventures Limited, Auckland (NZ)

( * ) Notice: Subject to any disclaimer, the term of this patent is extended or adjusted under 35 U.S.C. 154(b) by 946 days.

(21) Appl. No.: 16/763,832

(22) PCT Filed: Nov. 13, 2018

(86) PCT No.: PCT/NZ2018/050161
§ 371 (c)(1),
(2) Date: May 13, 2020

(87) PCT Pub. No.: WO2019/093910
PCT Pub. Date: May 16, 2019

(65) Prior Publication Data
US 2020/0282171 A1     Sep. 10, 2020

(30) Foreign Application Priority Data
Nov. 13, 2017 (NZ) ........................ 737269

(51) Int. Cl.
*A61M 16/10* (2006.01)
*A61M 16/00* (2006.01)
(Continued)

(52) U.S. Cl.
CPC ...... *A61M 16/1045* (2013.01); *A61M 16/022* (2017.08); *A61M 16/06* (2013.01); *C08F 251/02* (2013.01); *A61M 2016/0024* (2013.01); *A61M 2205/3368* (2013.01); *A61M 2205/36* (2013.01); *A61M 2205/8206* (2013.01)

(58) Field of Classification Search
CPC .................................................. A61M 16/1045
See application file for complete search history.

(56) References Cited

U.S. PATENT DOCUMENTS

| 4,601,287 A | * | 7/1986 | Royce, Jr. | ............... A62B 23/02 128/206.23 |
| 5,109,471 A | * | 4/1992 | Lang | ..................... A61M 16/16 392/395 |

(Continued)

FOREIGN PATENT DOCUMENTS

| CN | 106659968 A | 5/2017 |
| WO | 2015051126 A1 | 4/2015 |

OTHER PUBLICATIONS

Chinese Office Action dated Jan. 18, 2023, Chinese Application No. 201880086393.9 filed on Nov. 13, 2017, 11 pages.
(Continued)

*Primary Examiner* — Michael J Tsai
(74) *Attorney, Agent, or Firm* — Conley Rose P.C.

(57) ABSTRACT

A moisture exchange fabric is disclosed the fabric comprising: a substrate fabric; a polymer having lower critical solution temperature (LCST) of between 25° C. and 39° C. bonded to the substrate fabric; and a filament sewed into the substrate fabric. Also disclosed is a humidifying apparatus using the moisture exchange fabric.

20 Claims, 16 Drawing Sheets

(51) Int. Cl.
*A61M 16/06* (2006.01)
*C08F 251/02* (2006.01)

(56) References Cited

U.S. PATENT DOCUMENTS

| | | | |
|---|---|---|---|
| 5,462,048 A * | 10/1995 | Lambert | A61M 16/1045 128/201.13 |
| 6,330,883 B1 | 12/2001 | Berger | |
| 8,459,259 B2 * | 6/2013 | Klasek | A61M 16/108 128/203.26 |
| 2001/0042546 A1 * | 11/2001 | Umeda | A61M 11/047 128/203.26 |
| 2004/0099268 A1 | 5/2004 | Smith et al. | |
| 2016/0250438 A1 | 9/2016 | Harwood et al. | |
| 2017/0172227 A1 | 6/2017 | Fan et al. | |
| 2017/0282120 A1 | 10/2017 | Uramoto et al. | |

OTHER PUBLICATIONS

Daniel Wandera, et al., "Modification of ultrafiltration membranes with block copolymer nanolayers for produced water treatment: The roles of polymer chain density and polymerization time on performance", Journal of Membrane Science 403-404 (2012) 250-260, Mar. 5, 2012.

Hengrui Yang, et al., "Temperature-Triggered Collection and Release of Water from Fogs by a Sponge-Like Cotton Fabric", Advanced Materials 2013, 25, 1150-1154, Jan. 9, 2013.

Marta A Cooperstein, et al., "Assessment of cytotoxicity of (N-isopropyl acrylamide) and Poly(N-isopropyl acrylamide)-coated surfaces", Biointerphases 8, 19 (2013); https://doi.org/10.1186/1559-4106-8-19, Aug. 7, 2013.

Hengrui Yang, et al., "In-situ study of the structure and dynamics of thermo-responsive PNIPAAm grafted on a cotton fabric", Polymer 53(16), 3577-3586, Jun. 7, 2012.

Kyle N. Plunkett, et al., "PNIPAM Chain Collapse Depends on the Molecular Weight and Grafting Density", Langmuir, 22(9), 4259-4266, Feb. 7, 2006.

* cited by examiner

FABRIC AND METHOD OF MANUFACTURING

CROSS-REFERENCE TO RELATED APPLICATIONS

The present application is a filing under 35 U.S.C. 371 as the National Stage of International Application No. PCT/NZ2018/050161, filed Nov. 13, 2018, entitled "FABRIC AND METHOD OF MANUFACTURING," which claims priority to New Zealand Application No. 737269 filed with the Intellectual Property Office of New Zealand on Nov. 13, 2017, both of which are incorporated herein by reference in their entirety for all purposes.

FIELD

This invention relates to a fabric, a respiratory humidifying device, and a self-humidified mask and further relates to a method of manufacturing a fabric, a respiratory humidifying device and a self-humidified mask.

BACKGROUND

Nasal air-conditioning is a transport process which controls the temperature and the humidity of the air during respiration process. During inspiration, air is in contact with the warm and moist nasal mucosa and is rapidly warmed and humidified (Hanna & Scherer, 1986). This heat and mass transfer process is produced because a driving force is created by the difference in temperature and water concentration between the inspired air, which is at room temperature and humidity (Wolf, Naftali, Schroter, & Elad, 2004), and the mucus layer, which is at body temperature. The mucus layer is composed of 95% water and 5% of carbohydrate, protein, lipid and inorganic material (Yeager, 1971). (Hanna & Scherer, 1986).

Under normal breathing conditions temperature and absolute humidity corresponds to 22° C. and 10 mgH$_2$O/L on nares, 31-33° C. and 26-32 mgH$_2$O/L on larynx, 34° C. and 34-38 mgH$_2$O/L on mid-trachea, and 37° C. and 44 mgH$_2$O/L on main bronchi (Wolf et al., 2004). Optimal gas exchange occurs when air reaches the lungs at 37° C. with 100% relative humidity which corresponds to 44 mgH$_2$O/L. This is known as isothermal saturation boundary (ISB). Under this condition the physical properties of the mucus layer are optimized and the mucociliary transport is maximum.

Mucociliary transport is a self-clearing mechanism of the respiratory system. The mucus covering the respiratory epithelium traps particulate material and pathogens, and the coordinated ciliary activity moves the layer and remove the particles trapped. In the nose the mucus is moved towards the pharynx, and in the tracheobronchial tree the mucus is moved toward and through the larynx and swallowed. An alteration in mucus rheology, which can be caused by a range of pathophysiological conditions, can affect the mechanical coupling of the cilia with the overlying mucus called airway surface liquid layer (Atsuta & Majima, 1998).

Breathing devices, such as asthma nebulizers, positive airway pressure devices, respirators or even tracheotomy, are used to restore or provide a proper respiration cycle in some patients. These therapies disturb the natural lubrication and normal air conditioning process because there is an increase in pressure and turbulent effect, or the nasal cavity, which is the most important air conditioning part, is bypassed. Breathing devices, can cause drying and trauma of the mucosa where ciliated cells are inactivated and reduced (Malik & Kenyon, 2004). Therefore, inspired air has to be warmed and humidified in order to reach the lungs at 37° C. with 100% relative humidity, and maintain an optimum mucociliary transport.

An object of the invention is to develop an improved respiratory humidifying device able to uptake water from expiration and release it into the inspiration flow or to at least provide the public or industry with a useful choice.

SUMMARY

According to one example embodiment there is provided a moisture exchange fabric comprising:
  a substrate fabric;
  a temperature-responsive polymer having lower critical solution temperature (LCST) of between 25° C. and 39° C. bonded to the substrate fabric; and
  a filament sewed into the substrate fabric.
Preferably the substrate fabric is a hydrophilic fabric.
Preferably the substrate fabric is selected from the group consisting of natural fibres and processed fibres.
Alternatively, the substrate fabric is selected from the group consisting of cotton, linen, chitin, chitosan, rayon, polyvinyl alcohol (PVA), and polypropylene
Preferably the polymer is PNIPAM.
  More preferably the LCST is between 28° C. and 39° C.
  More preferably the LCST is between 30° C. and 34° C.
  More preferably the LCST is 32° C.
Preferably the polymer is selected from the group consisting of Elastin-like oligo- and polypeptides, Poly(acrylic acid-co-acrylamide), Poly(methyl vinyl ether) (PMVE), Poly(oxazoline)s, Poly(N-vinyl caprolactam) (PVC), and Poly(N-alkylacrylamide)s.

According to another example embodiment there is provided a respiratory humidifying apparatus comprising:
  a moisture exchange fabric positioned so that a respiratory system inspiration and expiration airflow is in contact with the moisture exchange fabric, the moisture exchange fabric comprising:
  a substrate fabric, and
  a temperature-responsive polymer having lower critical solution temperature (LCST) of between 25° C. and 39° C. bonded to the substrate fabric;
  a heater for heating the moisture exchange fabric;
  a power supply for supplying power to the heater; and
  a controller controlling the supply of power to the heater such that during inspiration when the moisture exchange fabric is heated and moisture is added to the incoming air such that humid air is provided to a user and during expiration the moisture exchange fabric extracts moisture from the air.
Preferably the power supply is a battery.
Preferably the controller switches the power on and off according to typical inspiration and expiration phases is a switching unit.
Preferably the controller is a switching unit.
Preferably the apparatus is used for CPAP therapy.

According to another example embodiment there is provided a method of controlling the water vapour release and absorption of a moisture exchange fabric providing humidified air to a user positioned so that a respiratory system inspiration and expiration airflow is in contact with the moisture exchange fabric, the moisture exchange fabric comprising a substrate fabric and a temperature responsive polymer having a lower critical solution temperature (LCST) of between 25° C. and 39° C. bonded to the substrate fabric, the method comprising using a controller to control a heater by controlling the supply of power to the heater such that during inspiration the moisture exchange fabric is heated and moisture is added to incoming air such that humid air is provided to a user and during expiration the moisture exchange fabric extracts moisture from the air.

It is acknowledged that the terms "comprise", "comprises" and "comprising" may, under varying jurisdictions, be attributed with either an exclusive or an inclusive meaning. For the purpose of this specification, and unless otherwise noted, these terms are intended to have an inclusive meaning—i.e., they will be taken to mean an inclusion of the listed components which the use directly references, and possibly also of other non-specified components or elements.

Reference to any document in this specification does not constitute an admission that it is prior art, validly combinable with other documents or that it forms part of the common general knowledge.

BRIEF DESCRIPTION OF THE DRAWINGS

The accompanying drawings which are incorporated in and constitute part of the specification, illustrate embodiments of the invention and, together with the general description of the invention given above, and the detailed description of embodiments given below, serve to explain the principles of the invention, in which.

DETAILED DESCRIPTION

Thermo-responsive polymers such as Poly n-isopropylacrylamide have the ability to respond to a change in temperature and are used for biomedical applications including drug delivery, tissue engineering and gene delivery. Temperature-responsive polymers exhibit a volume phase transition at a certain temperature, which causes a sudden change in the solvation state. Polymers, which become hydrophobic upon heating, have a so-called Lower Critical Solution Temperature (LCST). Systems, which become hydrophilic upon heating, have an Upper Critical Solution Temperature (UCST). LCST and UCST systems are not restricted to an aqueous solvent environment, but only the aqueous systems are of interest for biomedical applications (Matanović, Kristl, Grabnar, 2014).

Typical LCST polymers are based on N-isopropylacrylamide (NIPAM), N,N-diethylacrylamide (DEAM), methyl vinyl ether (MVE), and N-vinylcaprolactam (NVCl) as monomers. A typical UCST system is based on a combination of acrylamide (AAm) and acrylic acid (AAc) and its corresponding co-polymers.

Poly(N-alkylacrylamide)s such as poly(N-isopropylacrylamide) (PNIPAM) or poly(N,N-diethylocrylamide) (PDEAM)

PNIPAM is the most prominent candidate as thermo-responsive polymer even though a second polymer in this class has a nearly identical transition temperature: PDEAM. However, the transition temperature of PDEAM depends on the tacticity of the polymer, which is in contrast to PNIPAM. Its biocompatibility and the position of the LCST at 32-33° C. makes PNIPAM a very interesting material, e.g. for controlled release application. The LCST of PNIPAM is independent of the molecular weight and the concentration, but it can be changed upon shifting the hydrophilic/hydrophobic balance. PNIPAM copolymers have been mainly studied for the oral delivery of calcitonin and insulin. The peptide or hormone is immobilised in polymeric beads, which stay stable while passing through the stomach. Then in the alkaline intestine the beads disintegrate, and the drug is released (Matanović, Kristl, Grabnar, 2014).

Figure 3:
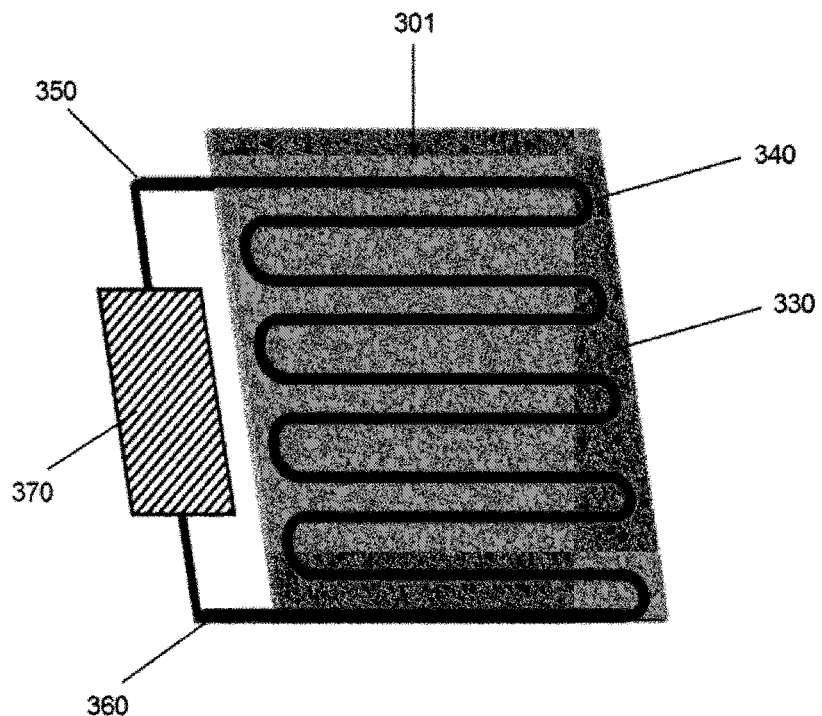
FIG. 3 is an example of the fabric of the present invention with a filament incorporated.

FIG. 3 illustrates respiratory humidifying device 301 according to an example embodiment. The respiratory humidifying device 301 comprises a fibrous cotton fabric polymerized with Poly (N-isopropylacrylamide) (PNIPAM) 330 and with a resistor filament 340 sewed into the fibrous PNIPAM-Cotton 330.

PNIPAM is an eco-friendly temperature-sensitive polymer which undergoes a coil-to-globule transition (hydrophilic-to-hydrophobic) in aqueous solution at a specific temperature of 32° C. called lower critical solution temperature (LCST). Poly n-isopropylacrylamide may be abbreviated as PNIPAM, PNIPAm, pNIPAm, PNIPA, pNIPA, PNIPAAm, pNIPAAm, PNIPAA, pNIPAA.

Below the lower critical solution temperature and in the presence of water, the PNIPAM-molecules are predominantly hydrophilic and the amide-groups tend to form intermolecular hydrogen bonds with the surrounding water molecules.

Above the lower critical solution temperature, the hydrophobic isopropyl-methyl groups tend to establish polymer-polymer interactions, which are energetically more favourable at higher temperatures. This transition is accompanied with a change from coil-to-globule configuration. PNIPAM is commonly used as copolymer in stimuli-responsive membranes, which change their physicochemical properties in response to changes in their environment such as temperature.

Alternative polymerizes are discussed below (Matanović, Kristl, Grabnar, 2014). While in the example embodiment PNIPAM is used other suitable polymerizes could be used.

Poly(N-vinyl caprolactam) (PVC)

PVC has not been studied as intensively as PNIPAM, but it also possesses very interesting properties for medical and biotechnological applications, e.g. solubility in water and organic solvents, biocompatibility, high absorption ability and a transition temperature within the settings of these applications of 33° C.

Poly(oxazoline)s such as Poly(2ethyl2oxazoline) (PEtOx) or poly(2isopropyl2oxazoline) (PIPOx)

Poly(N-ethyl oxazoline)s have a transition temperature around 62° C., which is too high for any drug delivery application. Recently a double thermoresponsive system was prepared by graft polymerisation of EtOx onto a modified PNIPAM backbone. Currently these systems are explored for their potential in drug delivery, because they tend to aggregate micelles above the LCST.

Poly(methyl vinyl ether) (PMVE)

Poly(methyl vinyl ether) has a transition temperature at exactly 37° C., which makes it very interesting for biomedical application. The polymer exhibits a typical type III demixing behaviour, which is in contrast to the thermal behaviour of PNIPAM. PMVE has to be synthesized by cationic polymerisation using inert condition. Nucleophiles like alcohol or amino groups cannot be tolerated during the synthesis, which limits the potential of PMVE.

Poly(acrylic acid-co-acrylamide) such as Polyacrylic Acid (PAAc) or Polyacrylamide (PAAm)

An interpenetrating network of poly(acrylic acid) and polyacrylamide is one of the few examples of a system with UCST behaviour within the biomedical setting. The transition temperature is at 25° C. The UCST behaviour is caused by the cooperative effects coming from the hydrogen bonding between AAc and AAm units.

Elastin-Like Oligo- and Polypeptides such as Poly(GVGVP) poly(pentapeptide) of Elastin (G: Glycine, V: Valine, and P: Proline)

Polypeptides can also show LCST behaviour, when hydrophilic and hydrophobic residues are balanced well. A polymer made out of the pentapeptide GVGVP as repeating unit exhibits a volume phase transition at 30° C., which is the hydrophobic folding and assembling transition. Below the phase transition, water molecules are structured around the polymer molecule; the attractive forces weaken upon heating and they finally go into the bulk phase.

The temperature-responsive polymer (with its specific LCST) and the substrate material should be selected according to the application, the specific design and the practical environmental conditions such as temperature and humidity. The LCST of a specific thermo-sensible polymer can be slightly modified during the polymerization process by varying the grafting density or the chain length. This The exemplary embodiment is designed for a room temperature between 20° C. and 25° C., and around 50% of relative humidity. The thermo-sensible polymer and its LCST is chosen to be above the room temperature to avoid a cooling system in the design, PNIPAM with LCST at 32° C. For similar practical conditions, LCST is preferably to above room temperature, between 25° C. and 39° C., more preferably the LCST is between 28° C. and 39° C. even more preferably the LCST is between 30° C. and 34° C. and most preferably the LCST is about 32° C.

Figure 1:
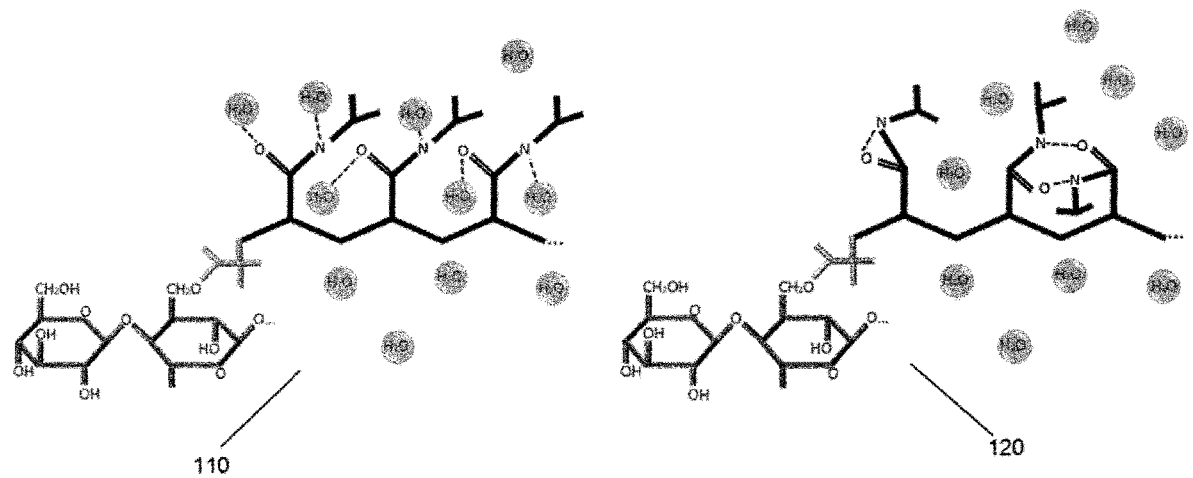
FIG. 1 illustrates the chemical behaviour of the PNIPAM-Cotton fabric of the present invention at temperatures above and below 32° C.

Referring to FIG. 1 the absorption and desorption process is outlined. Below 32° C. (lower critical solution temperature) the polymer 110 has a coil structure and hydrophilic state and form inter-molecular hydrogen bonds between oxygen and nitrogen, and the surrounding water molecules. Above lower critical solution temperature the polymer 120 has a globule structure and hydrophobic state and stablish polymer-polymer interactions between oxygen and nitrogen and release the water molecules previously absorbed.

The structural changes of a temperature-responsive polymer (PNIPAM) combined with the highly rough surface of a fibrous material, leads to reversible and repeatable switching between two extreme wettability states, superhydrophobic and superhydrophilic. This PNIPAM-Cotton fabric 330 is able to absorb water from a humid environment, below the lower critical solution temperature and release it upon a temperature change at constant humid air flow.

To create the PNIPAM-Cotton material 330, a cotton fabric is polymerized by PNIPAM (PNIPAM-Cotton fabric) and a resistor filament 340 is sewed in. Other fibrous materials such as natural fibres (Cotton, Linen, Chitin or Chitosan between others), synthetic or processed fibres (Rayon, Polyvinyl alcohol (PVA), or Polypropylene (PP) between others) or a mix could be used. Hydrophilic fibres with a high concentration of alcohol groups are desirable for the exemplary polymerization process described.

The resistor filament 340 is connected to a power supply 370 to create a respiratory humidifying device 301.

Figure 9A:
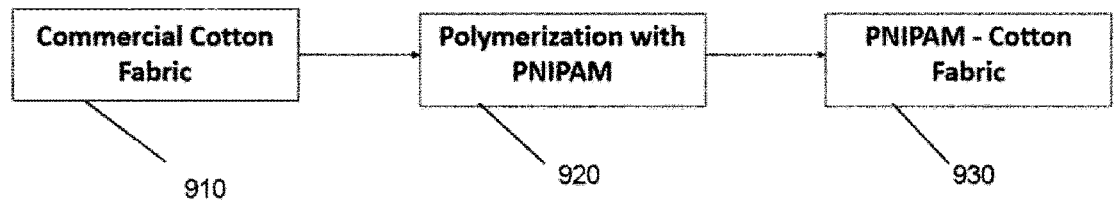
FIG. 9A is a flow diagram illustrating the grafting process of the fabric of the present invention.
Figure 9B:
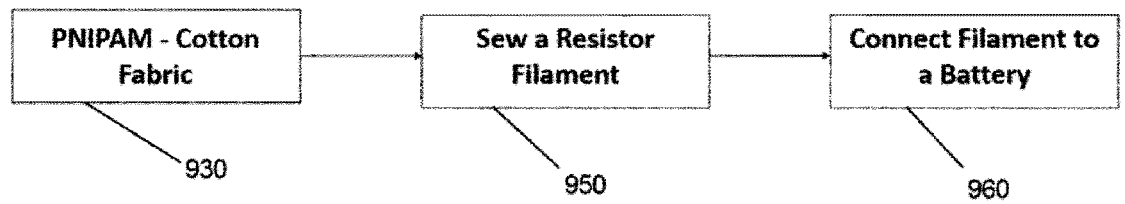
FIG. 9B is a flow diagram illustrating the process of incorporating the filament into the fabric of the present invention.

This process is outlined in FIGS. 9A and 9B.

Figure 12A:
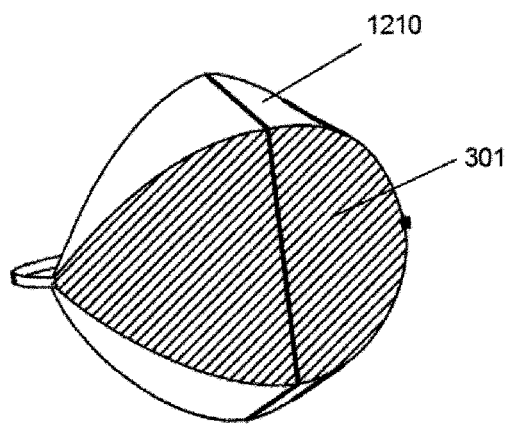
FIG. 12A is a front view of a further disposable exemplary mask incorporating the respiratory humidifying device.
Figure 12B:
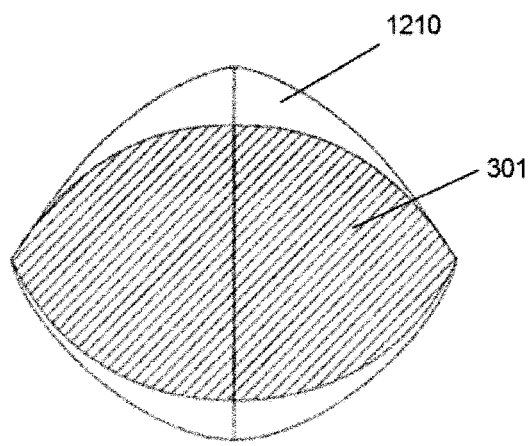
FIG. 12B is a partial front view of a further disposable exemplary mask incorporating the respiratory humidifying device.
Figure 12C:
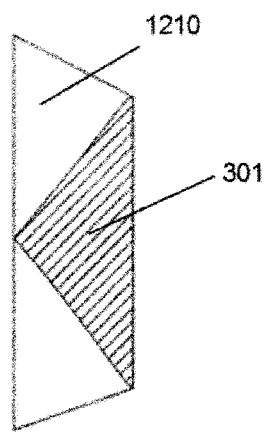
FIG. 12C is a side view of a further disposable exemplary mask incorporating the respiratory humidifying device.
Figure 13A:
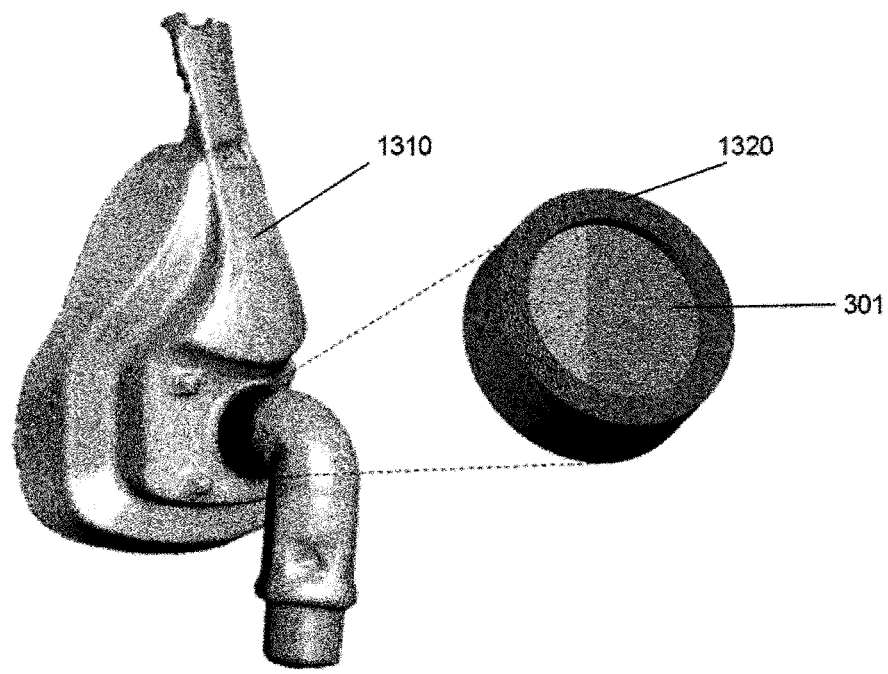
FIG. 13A is a front view of an exemplary mask incorporating the respiratory humidifying device as a filter.
Figure 13B:
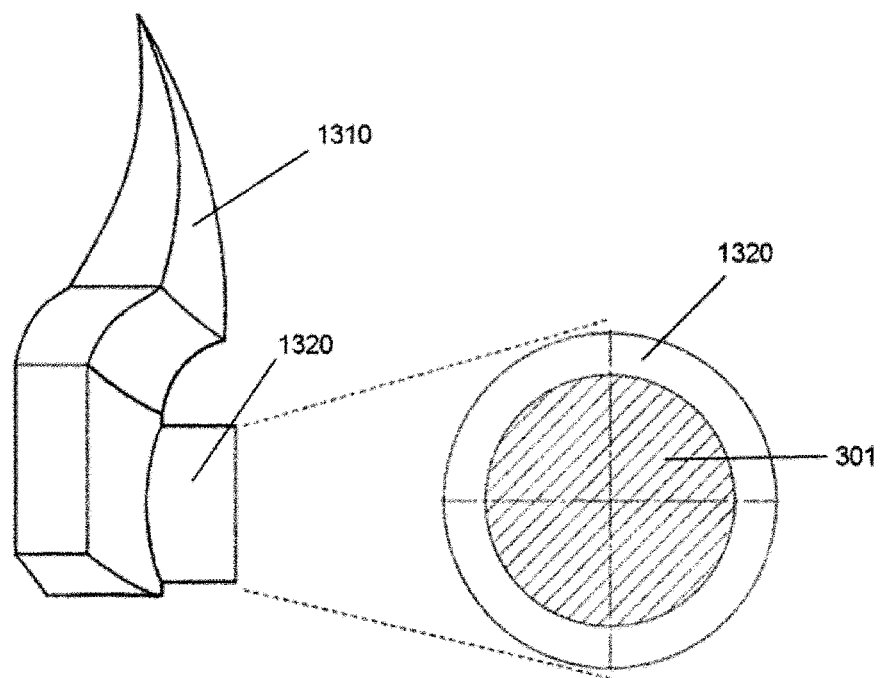
FIG. 13B is a front view of an exemplary mask incorporating the respiratory humidifying device as a filter.

The respiratory humidifying device 301 is placed at the inlet/outlet of the respiratory system in order to be in contact with the inspiration and expiration airflow. Various example embodiments of a mask with the respiratory humidifying device are illustrated in FIGS. 11A-D, 12A-C and 13A-B. In FIGS. 11A-D a commercial mask 1110 has the respiratory humidifying device 301 covering the inside of the mask. In FIGS. 12A-C a disposable mask is composed by 2 pieces of plain fabric 1210 and the respiratory humidifying device 301. In FIGS. 13A-B a commercial mask 1310 has the respiratory humidifying device 301 inserted as a filter 1320.

In use during expiration, no current is provided to the respiratory humidifying device 301 filament 340 in order to keep the respiratory humidifying device 301 at room temperature, typically below lower critical solution temperature. Under these conditions PNIPAM-molecules are predominantly hydrophilic and the amide-groups form inter-molecular hydrogen bonds with the surrounding water molecules.

Expiration flow is generally at 100% relative humidity and the PNIPAM-Cotton material is moisture saturated and absorbs the maximum number of water molecules.

When the expiration flow has ended, (after three seconds approximately) and inspiration flow starts, the power supply 370 is switched on passing current though the resistor filament 340. Depending on the voltage and intensity provided, the PNIPAM-cotton material is heated up to a temperature above lower critical solution temperature. Under these conditions the hydrophobic isopropyl-methyl groups tend to establish polymer-polymer interactions and the water molecules previously absorbed are released into the inspiration airflow. This airflow was originally at room conditions, but after passing through the respiratory humidifying device 301 the temperature and humidity are increased.

Figure 16:
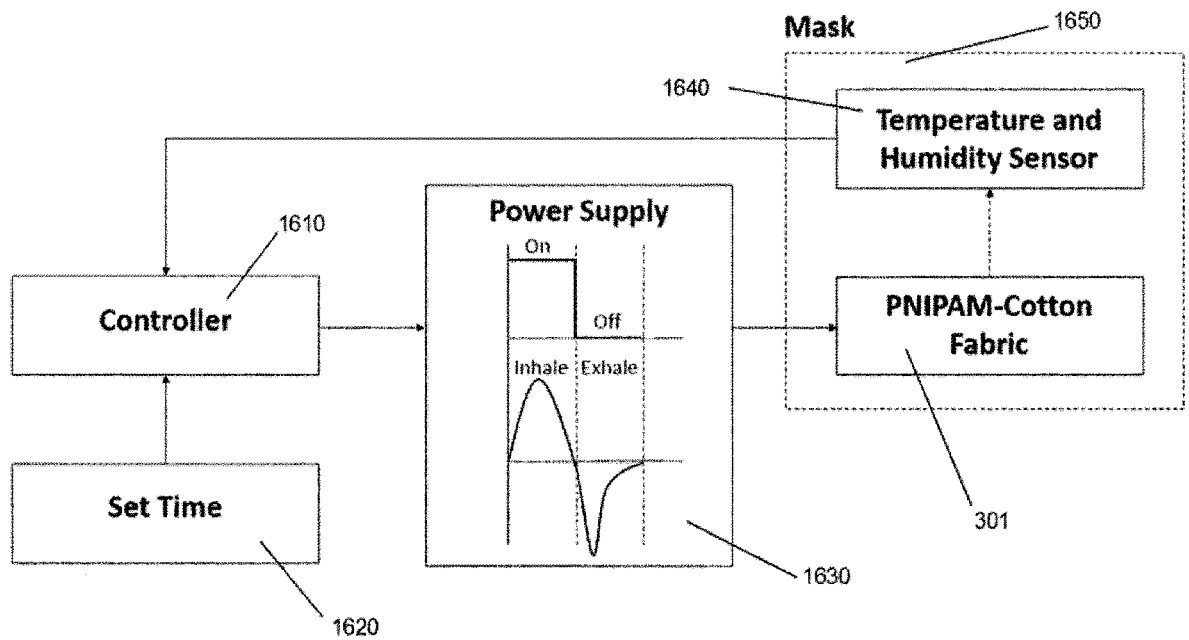
FIG. 16 is a flow diagram illustrating the process of tuning the behaviour of the power supply for each patient.

This process is adjusted for each patient using the respiratory humidifying device 301 as described in FIG. 16. An initial switch time 1620 is set to the power supply 1630. The measurement take place inside a mask 1650 containing the PNIPAM-Cotton Fabric 301 and a temperature and humidity sensor 1640. This data is controlled 1610 in order to adjust the power supply switch time to be on during inhalation and off for exhalation.

Polymerization Process for an Exemplary Embodiment:

To create the PNIPAM-Cotton material 330 a commercial cotton fabric is used as substrate. As discussed above other suitable substrates and temperature-responsive polymers could be used. A cotton fibre is typically composed of approximately 90% of cellulose $(C_6H_{10}O_5)n$, which is an organic polysaccharide consisting of a linear chain of several β(1→4) linked D-glucose units. Bare cotton dimensions are in 3 mm height, 5 cm width, and 5 cm depth, but other sizes may of course be used. The aim is to cover the hydrophilic surface of the cotton fabric with the PNIPAM polymer layer using an atom transfer radical polymerization (ATRP) method. With this method, it is possible to graft a small percentage of PNIPAM brushes directly from the cotton fabric surface. The bare-cotton fabric becomes fully covered with a thick and rough PNIPAM layer, which increases the diameter of the fibres, and the polymer chains grow from the fibres surface with a concentric orientation creating a highly rough surface at the micrometre level. The process could take up to two weeks.

The materials and equipment used to synthesize the PNIPAM-Cotton material are the following:

commercial cotton fabric, commercial soap, distilled water, ethanol (99.5%), methanol (99.9%), dry tetrahydrofuran (THF) (99.8%), 4-(dimethylamino) pyridine (DMAP) (99%), triethylamine (TEA) (99%), bromoisobutyrate (BiB) (99%), copper(I)bromide (CuBr) (98%), N-Isopropylacrylamide (NIPAM) (99.5%), pentamethyldiethylenetriamine (PMDETA) (99%), ethyl 2-(bromomethyl) acrylate (EBMA) (98%), dimethylformamide (DMF) (99.8%), deuterated 4-methanol (Methanol-d4) (99.96%) and sodium hydroxide (NaOH) (97%), nitrogen flow, vacuum/Incubator chamber, and a high precision balance.

Figure 2A:
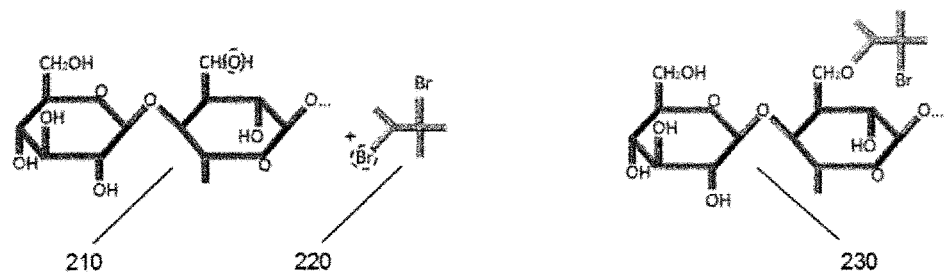
FIG. 2A illustrates the chemical composition of the fabric of the present invention before and after immobilization of the ATRP initiator.
Figure 2B:
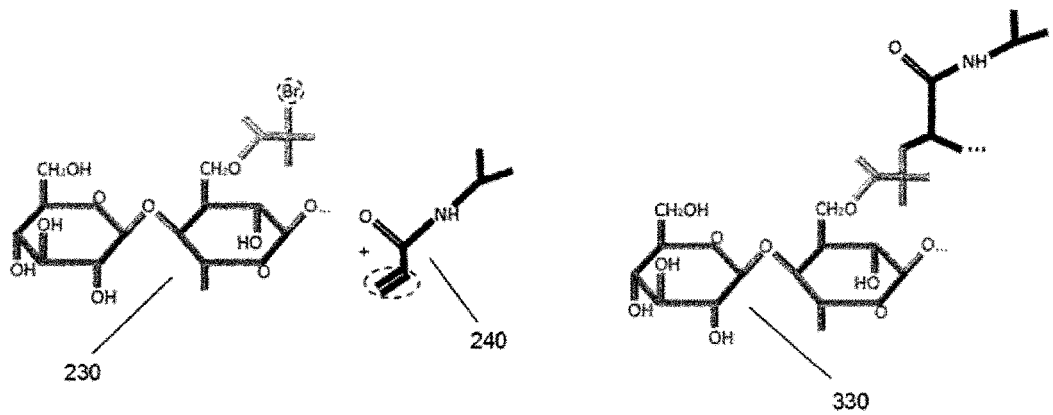
FIG. 2B illustrates the chemical composition of the fabric of the present invention after immobilization of the ATRP initiator and before and after grafting of an N-isopropylacrylamide.

The polymerization process has two important stages. Referring to FIGS. 2A and 2B the first stage is the immobilization of the ATRP-initiator on the cotton fabric 210, where one bromine atom of the initiator (bromoisobutyrate, BiB) 220 reacts with one alcohol group in cellulose molecules forming an oxygen-bromine covalent bond between the cotton fabric and the initiator agent 230.

In the second stage, the polymerization process starts from the monomer (NIPAM) 240 reacting with the second bromine of the initiator 230 already bonded to the cellulose molecules.

In an exemplary embodiment, the steps to reproduce the synthesis of PNIPAM-Cotton material are described below.

1. Immobilization of the ATRP-initiator on the cotton fabric:

Bare-cotton fabric is washed in an aqueous solution containing a commercial soap-detergent and under magnetic stirring for 1 hour, at ~100° C.

Bare-cotton is rinsed with water and ethanol.

This procedure is repeated three times, then the cotton is dried at 40° C. under vacuum for 24 h. Drying is important because the substrate material has to be completely dried to achieve a high reaction yield.

The bare cotton (0.828 g) 210 is then immersed in a solution containing 60 ml of tetrahydrofuran (THF), 2 ml of 4-(dimethylamino) pyridine (DMAP) and 2 ml of triethylamine (TEA). 1 ml of BiB was added into the mixture.

The reaction is kept at room temperature for 30 minutes under a nitrogen flow bubbling into the solution with slow magnetic stirring.

The reaction is sealed and kept at room temperature for 1 to 2 days with slow magnetic stirring.

The product (BiB-cotton) 230 is rinsed thoroughly and consecutively for 3 times with THF, ethanol and water, and finally dried at 40° C. under vacuum, for 24 hours.

2. Grafting of N-Isopropylacrylamide from the initiator-functionalized cotton fabric:

The initiator-modified cotton fabric (BiB-cotton) 230, 0.001 g of CuBr, 2 g of N-isopropylacrylamide (NIPAM) and 0.5 ml of pentamethyldiethylenetriamine (PMDETA) is introduce into a flask containing 60 ml of MeOH/$H_2O$ solution (3:1 v/v) 240.

The reaction is kept at room temperature for 30 minutes under a nitrogen flow bubbling into the solution with slow magnetic stirring.

The reaction is then sealed and kept at room temperature for 4 days with slow magnetic stirring.

After this period, the fabric is sequentially washed with methanol, ethanol and water to remove the residual monomers and catalyst complex.

The PNIPAM modified fabric (PNIPAM-cotton) 330 is finally dried under vacuum at 40° C. overnight.

Polymerization Process for a Further Exemplary Embodiment:

The first step is the substrate surface modification or the immobilization of the ATRP-initiator on the substrate material, where one bromine atom of the initiator (bromoisobutyrate, BiB) reacts with one alcohol group forming an oxygen-bromine covalent bond between the substrate and the initiator agent.

The methodology followed has been optimized to ensure the best temperature and reaction times as described below:

The substrate material was washed in an aqueous solution containing a commercial soap-detergent and under magnetic stirring for 1 hour, at 100° C. to remove dust and impurities. Then, it is rinsed with water acetone and ethanol.

This procedure is repeated three times.

The substrate material was dried at 80° C. under vacuum for 24 hours. This is a crucial step because the substrate material has to be completely dried to achieve a high reaction yield.

Each side of the substrate material was exposed to 234 nm UV light wavelength for 30 minutes in order to activate the alcohol functional groups.

Then the substrate was added into a round-bottom flask containing THF and a magnetic stirrer.

The flask was sealed, connected to an active nitrogen gas line and left in an ultrasonic bath for 30 minutes in order to remove the oxygen from the flask and generate an inert atmosphere.

Then, the flask was sealed with a nitrogen balloon to generate a positive pressure and a catalytic amount of DMAP, TEA and an excess of BiB were added into the solution.

The reaction was kept at 40° C. under magnetic stirring for 24 hours.

The ATRP-initiator or BiB-substrate product was rinsed thoroughly and consecutively for 3 times with THF, ethanol, acetone and water.

The BiB-substrate was dried at 80° C. under vacuum for 24 hours. As, stated before, this is a crucial step since the substrate material has to be completely dried to achieve a high reaction yield.

In the second stage, the polymerization process starts from the monomer (NIPAM) reacting with the second bromine of the ATRP-initiator already bonded to the substrate. There are two leading components in this reaction: PNIPAM and Copper bromide. The PNIPAM is the polymer going to be grafted for its properties. The Copper bromide is the ATRP catalyst. It switches its valence electrons from Cu I to Cu II and back. With this it can repeatedly attract and repel the second bromide of the BiB-substrate. The Br atom is replaced by a radical, which subsequently results in the reaction between the BiB-substrate and PNIPAM. The methodology followed has been optimized to ensure the best temperature and reaction times as described below:

A methanol/Milli-Q-water solution (30:10) was added into a round-bottom flask containing a magnetic stirrer.

The flask was sealed, connected to an active nitrogen gas line and left in an ultrasonic bath for 30 minutes in order to remove the oxygen from the flask and generate an inert atmosphere.

A catalytic amount of CuBr, NIPAM and the BiB-substrate were added into a schlenk flask. The flask was sealed and connected to an active nitrogen gas line to remove the oxygen and generate an inert atmosphere.

Then, the methanol/Milli-Q-water solution and PMDETA were added into the schlenk flask. The solution was frozen by liquid nitrogen and sequentially degassed by three freeze-vacuum-nitrogen-thaw cycles to remove the remaining oxygen. This is the most effective method of degassing a solvent.

The flask was connected to a vacuum line and immerse in liquid nitrogen until the solvent was completely frozen.

Then, a vacuum was generated for 2-3 minutes and the flask was removed from the liquid nitrogen to allow the solvent to thaw and any gas bubbles trapped in the solvent to escape into the headspace of the flask. This process was repeated three times.

The flask was filled with nitrogen and sealed with a balloon to generate a positive pressure.

The reaction was kept at 40° C. under magnetic stirring for 48 hours.

The PNIPAM-substrate product was rinsed thoroughly and consecutively for 3 times with ethanol, acetone and water and dried at 50° C. under vacuum for 24

As the PNIPAM-substrate material is synthetized to be in contact with the human breathing cycle and humidify the inspired gas by using recovered moisture from the expired gas. Hence, it is very important to purify the material and eliminate the traces of monomer, catalyst and solvent. The methodology followed to perform the extended purification step has been optimized to ensure the best temperature and reaction times as described below:

The PNIPAM-substrate was soxhlet extracted with methanol in reflux for 1 hour to remove the non-reacted monomer residue, the polymer absorbed at the surface but not covalently bonded and the remaining catalyst complex.

After the extraction procedure the PNIPAM-substrate was dried at 50° C. under vacuum for 24 hours and stored in an incubator at 50° C. to ensure dry conditions.

This optimized PNIPAM-Cotton fabric is able to achieve a water vapour release rate of 24.2±1.054%/min (mean±standard deviation, n=3), which corresponds to the weight percentage of water vapour released per minute, at a LCST of 32° C. This means that, below 32° C. the fabric absorbs the surrounding water vapour molecules and release them when the temperature is higher than 32° C. achieving a water vapour release rate up to 24.2±1.054%/min (mean±standard deviation, n=3).

Once the fabric 330 is created the PNIPAM-cotton material 330 is threaded/sewn with a resistor filament 340. While one method of creating the fabric has been described above may alternatives to create the fabric exist including: polymerizing the substrate fabric and sewing the resistor filament; polymerizing the substrate fibre and then sew the fibre and the resistor filament together; and synthetize the thermo-responsive polymer and the substrate at the same time in order to obtain a thermo-responsive synthetic fibre (PNIPAM/PVA for example) and then sew the fibre and the resistor filament together.

The filament 340 in an exemplary embodiment is cooper 15 Ω/m and 40 cm long and covers all the fibrous surface 330. The length of the filament 340 will of course depend on the size of the fabric 330. In this example, the filament 340 is sewn/threaded to form an S shape of 8 rows 5 cm long having a distance of 5-6 mm between each row as shown in FIG. 3. Both filament 340 ends are connected 350, 360 to a power supply 370 in order to provide current though the filament 340 and heat the fabric 330. The resulting temperature distribution on the PNIPAM-Cotton surface will vary according to the voltage delivered. For safe and safety reasons the voltage applied should not be higher than 12V and the temperature reached should be below 60° C. Depending on the properties of the filament used and the design (resistance at room temperature, resistivity and length) it is possible to calculate the relation between the temperature provided and the resistance using the following formula 1.

$$R = R_0(1 + \alpha(T - T_0)) \qquad (1)$$

Figure 4:
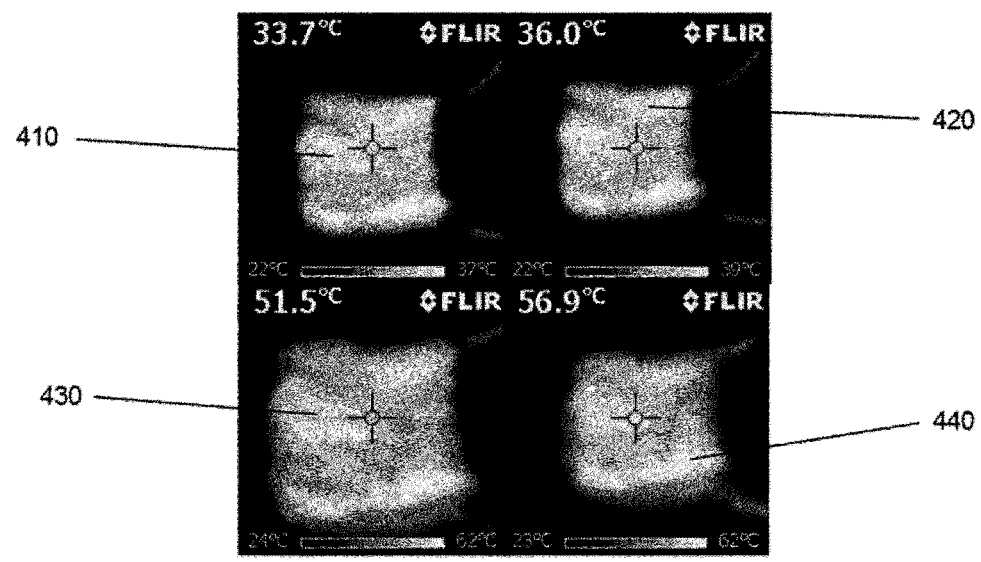
FIG. 4 is an infra-red image of the fabric at various temperatures.
Figure 14:
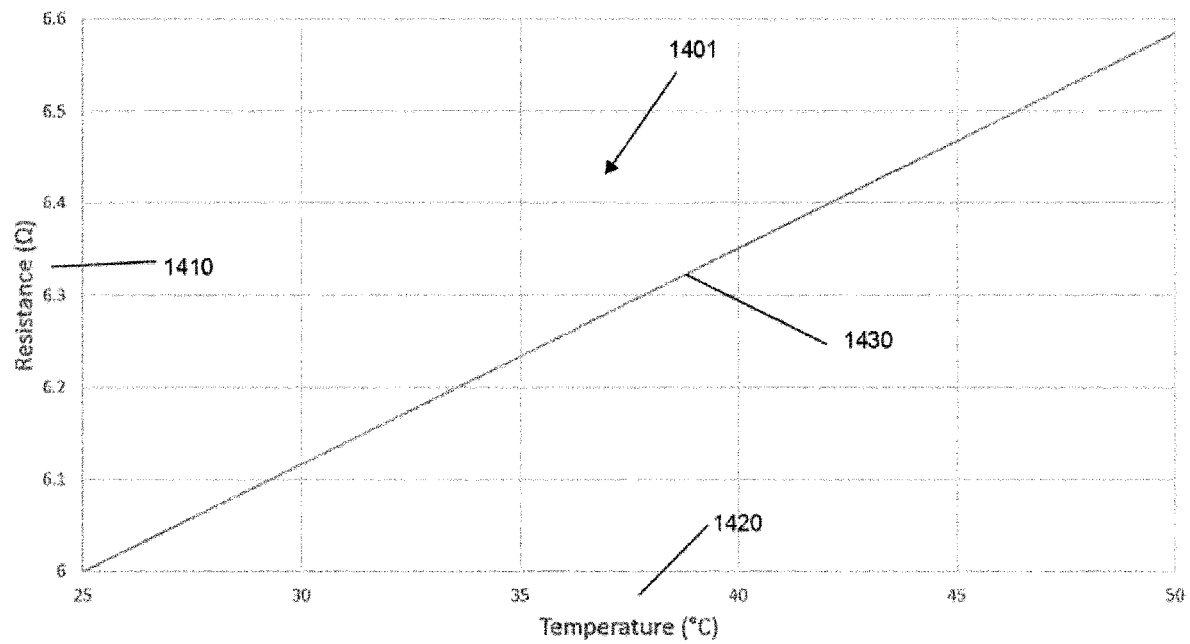
FIG. 14 is a calibration curve illustrating the linear relation between the resistance of the filament and the temperature provided.

Being $R_0$ the resistance at room temperature $T_0$, in this example 15 Ω/m using 0.4 m of cooper filament, so 6 Ω at 25° C. The temperature coefficient ($\alpha$) is a constant value of the conductor material used, 0.0039/° C. for cooper. The resulting plot 1401 is illustrated in FIG. 14. It is a linear relation 1430 between resistance 1410 and temperature 1420. Voltage and Current will be adjusted according to the value of resistance needed using a power supply regulator. The 'S' or zig zig shape and distance between the filament 340 rows was chosen in order to provide a fast heating response and a uniform temperature distribution on the PNIPAM-cotton material 330. Other shape may alternatively be used provided they result in even distribution of heat. The most preferred design was analysed using an Infra-Red Camera, and the resulting images are illustrated in FIG. 4. The response to heat is shown at 33.7° C., 410, 36° C., 420, 51.5° C. 430 and 56.9° C. 440.

The PNIPAM-Cotton material 330 is able to achieve a water vapour release rate of 24.2±1.054%/min (mean±standard deviation, n=3), which corresponds to the weight percentage of water vapour released per minute, at a LCST of 32° C. This means that, below 32° C. the fabric absorbs the surrounding water vapour molecules and release them when the temperature is higher than 32° C. achieving a water vapour release rate up to 24.2±1.054%/min (mean±standard deviation, n=3). These results showed no significant differences between the three samples synthetized, which proves repeatability of the results.

Figure 5:
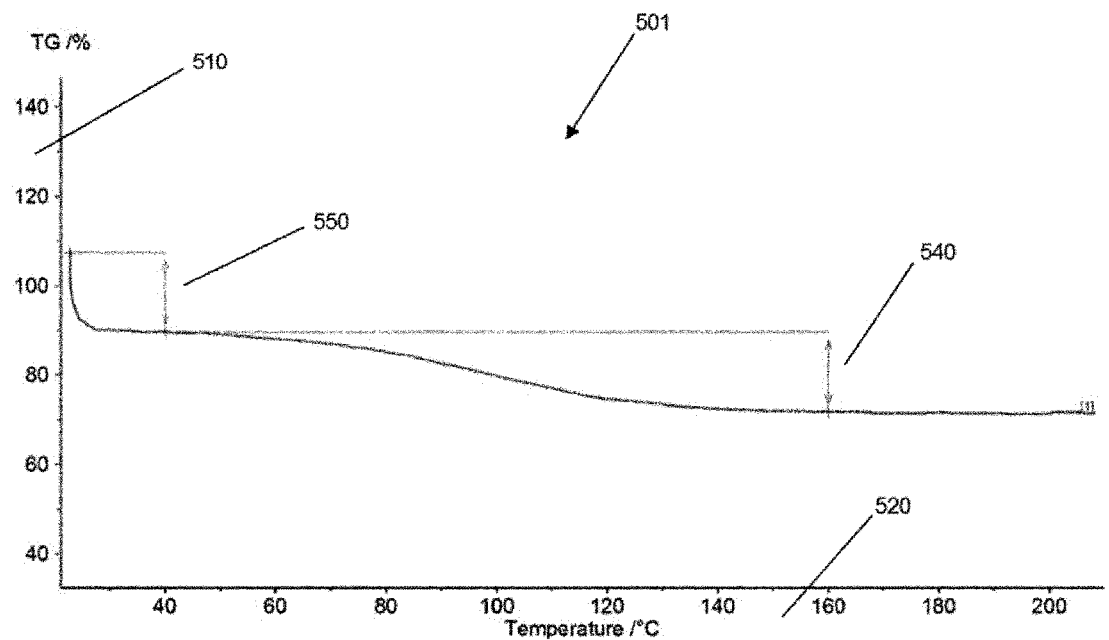
FIG. 5 is a thermogravimetric analysis graph the fabric of the present invention.

The respiratory humidifying device 301 was calibrated in order to determine the exact transition temperature of the synthetized PNIPAM-cotton material 330, and the relation between the percentage of water released and the temperature calculated. A thermogravimetric analysis is performed to quantify the % of mass change 510 as a function of temperature 520. The analysis starts at room conditions (50% of relative humidity and 20° C.) and increases the temperature until 200° C. while measures the mass change for each sample. The results illustrated 501 in FIG. 5 shows a decrease 550 of sample mass up to 40° C., after that it remains stable until 100° C. where the rest of water 540 is evaporated. This means that the transition temperature of this exemplary PNIPAM-cotton material 330 is set at 28° C.

Figure 6:
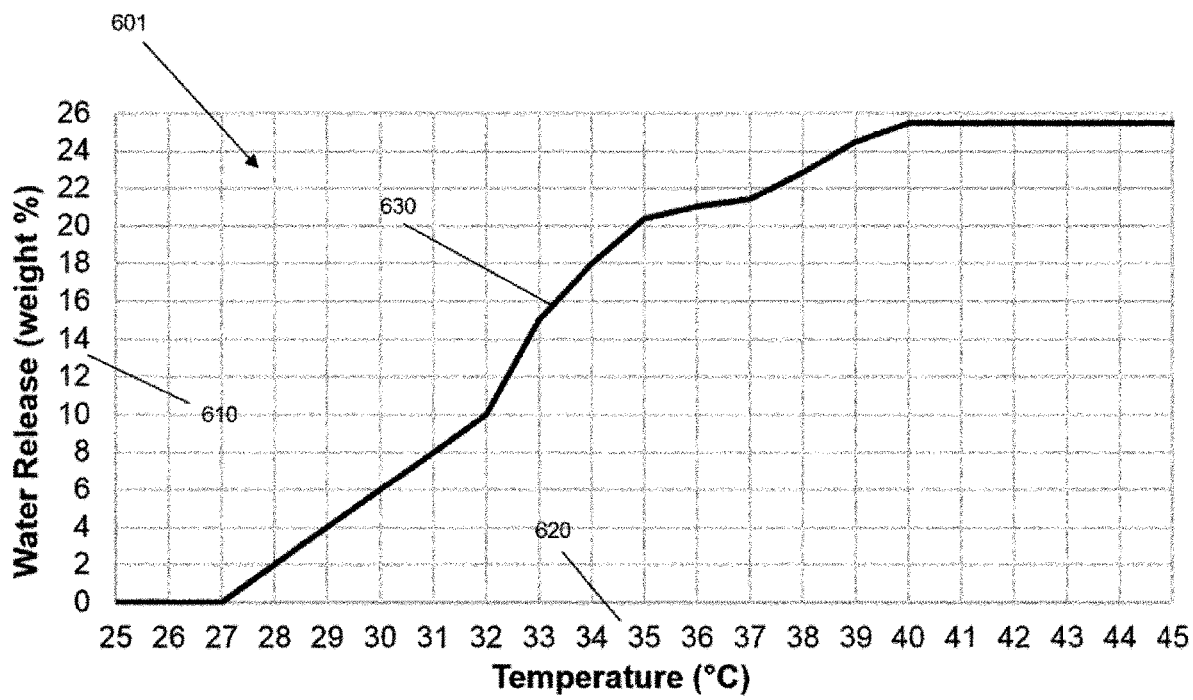
FIG. 6 is a graph illustrating the percentage of water released from the fabric of the present invention related to temperature.

A calibration curve 630 was developed after the evaluation of different samples as shown in the graph 601 of FIG. 6. The curve 630 provides the percentage of water released 610 as a function of the temperature 620 provided to the respiratory humidifying device 301. For example, 4 g of synthetized fabric heated above 40° C. is able to provide 1.02 g of water vapour or 4 g of synthetized fabric at 33° C. is able to provide 0.6 g of water vapour. Hence, the water vapour release can be adjusted depending on the temperature of the fabric. Hence, using this curve we will choose the operating temperature depending on the amount of water we want to provide into the system. With this temperature, we will determine the resistance using plot 1401 (seen in FIG. 14), voltage and current the power supply 370 needs to provide to the respiratory device 301.

The respiratory humidifying device 301 was tested on the human respiratory system. A facemask 1650 containing the respiratory humidifying device 301 composed by the PNIPAM-cotton material 330 and the resistor filament 340, a humidity and temperature sensor 1640 is used as described in FIG. 16. The power supply 370 was connected to the resistor filament 340. The power supply 370 provides a constant voltage and is adjusted using a timer to switch on/off according to typical inspiration and expiration phases. Optionally the switching time can be modified. During inspiration the power supply 370 is on in order to overcome the transition temperature (up to 28° C.) and to allow the fabric 330 to release the water molecules previously absorbed. During expiration the power supply 370 is off in order allow the fabric 330 temperature to reduce to room temperature.

Figure 7:
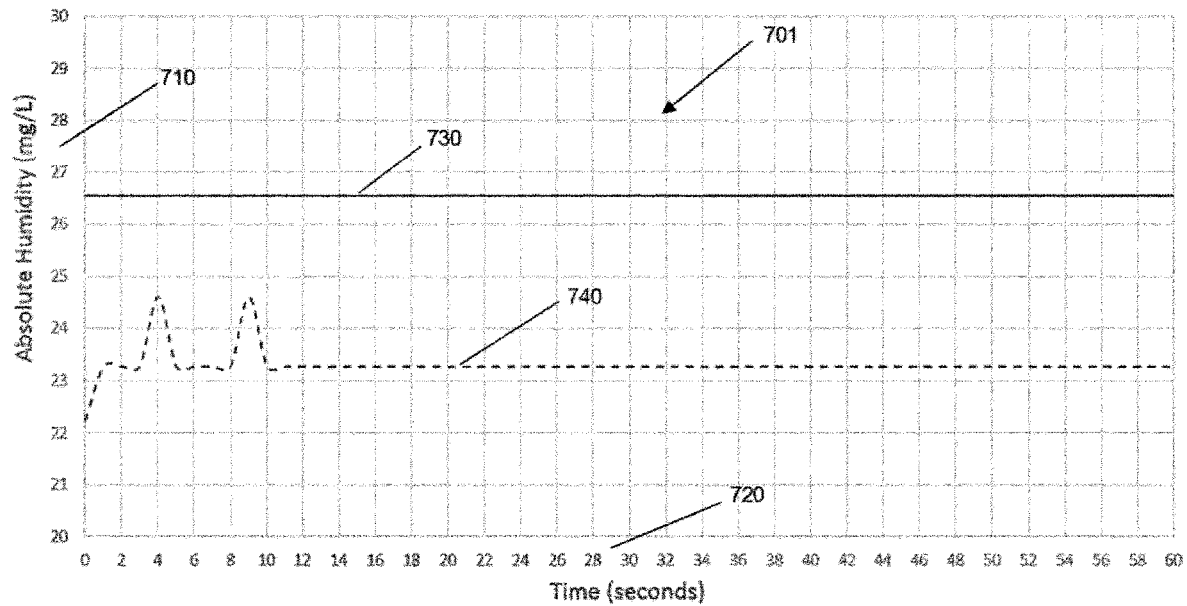
FIG. 7 is a graph illustrating the comparison between the humidity and temperature of the human respiratory airflow with and without the fabric of the present invention in the airflow.

As illustrated in the graph 701 of FIG. 7 a measurement was carried out without the respiratory humidifying device 301 operating in order to measure the absolute humidity 740 inside the mask under normal breathing conditions. After respiratory humidifying device 301 was introduced the absolute humidity 730 was again tested. FIG. 7 shows time 720 vs absolute humidity 710. The graph 801 illustrated in FIG. 8 also shows time 820 vs absolute humidity 810 and shows how long the respiratory humidifying device 301 takes to reach a constant relative humidity 830.

Figure 8:
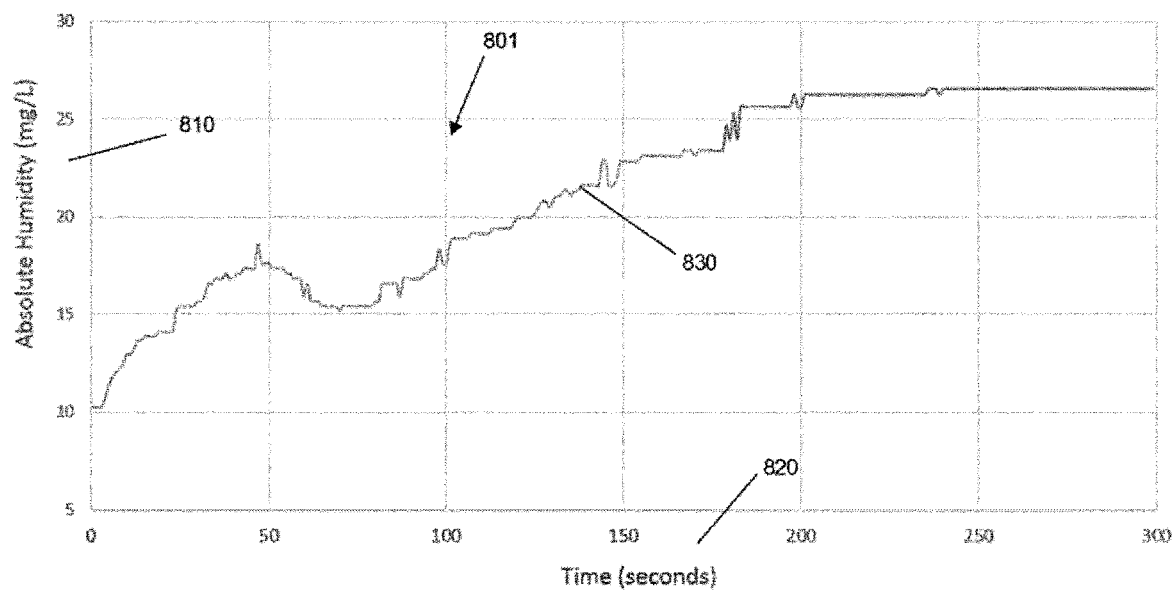
FIG. 8 is a graph illustrating the time taken for absolute humidity to stabilise with the fabric of the present invention in the airflow.

As demonstrated in the graph 801 of FIG. 8 the exemplary embodiment 301 is able to increase the absolute humidity to 26.5 mgH$_2$O/L in 4 minutes and stay constant whereas without the respiratory humidifying device 301 the absolute humidity is at 23.25 mgH$_2$O/L.

Figure 15:
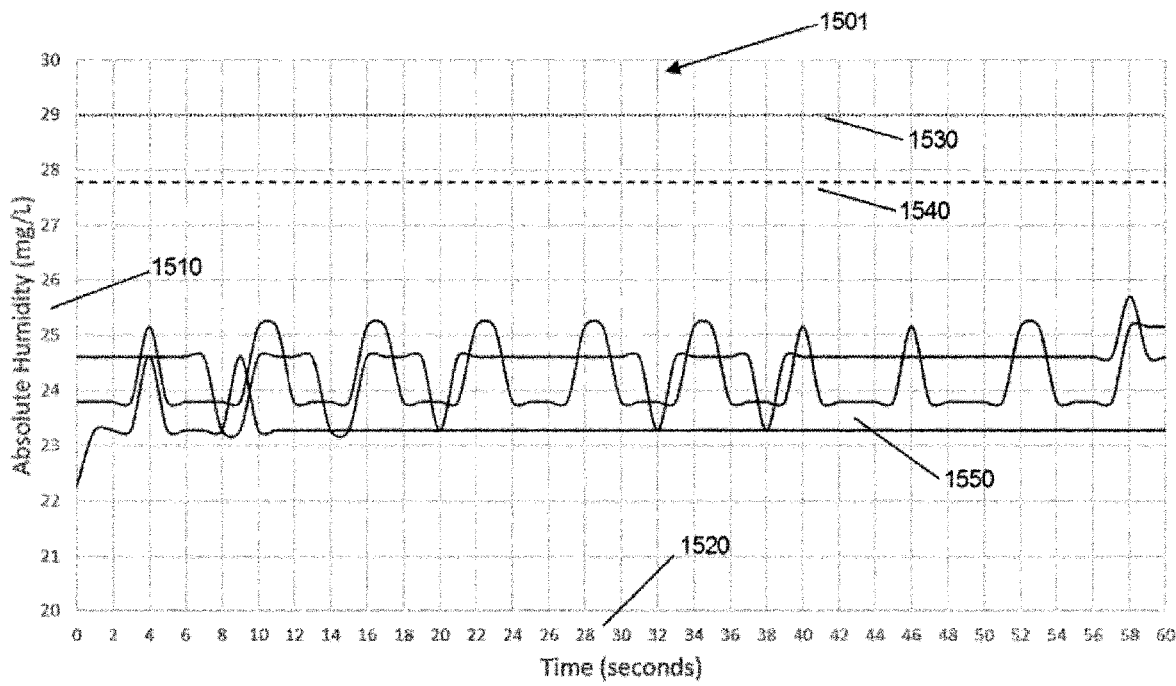
FIG. 15 is a graph illustrating the comparison between the humidity and temperature of the human respiratory airflow using a CPAP device with and without the commercial humidifier and with the respiratory humidifying device in the airflow.

Using the same setup outlined in FIG. 14, the respiratory humidifying device 301 was tested in a CPAP therapy. FIG. 15 shows a comparison 1501 between CPAP no humidified 1550, CPAP with a commercial humidifier 1530, and CPAP with the respiratory humidifying device 301 1540. The data illustrates the absolute humidity 1510 as a function of time 1520.

Figure 10:
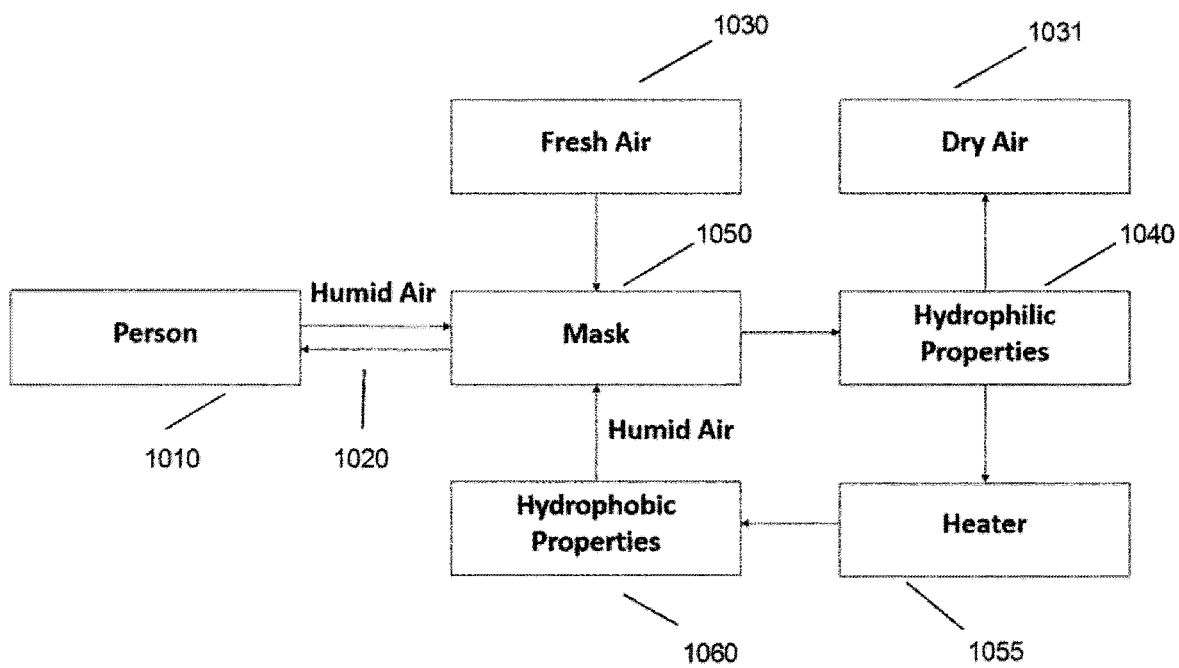
FIG. 10 is a flow diagram illustrating the humidification cycle.
Figure 11A:
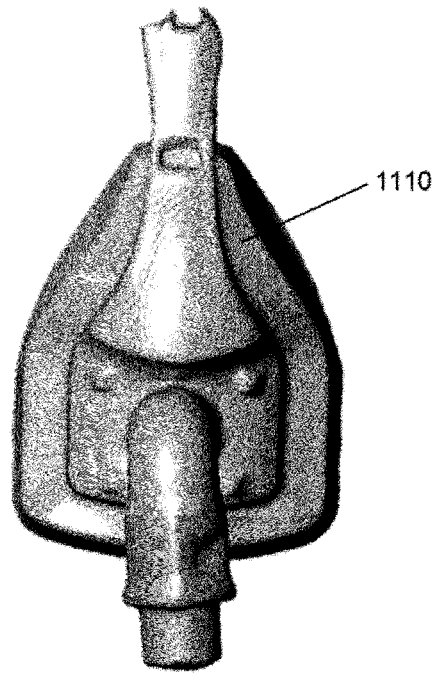
FIG. 11A is a front view of an exemplary mask incorporating the respiratory humidifying device.
Figure 11B:
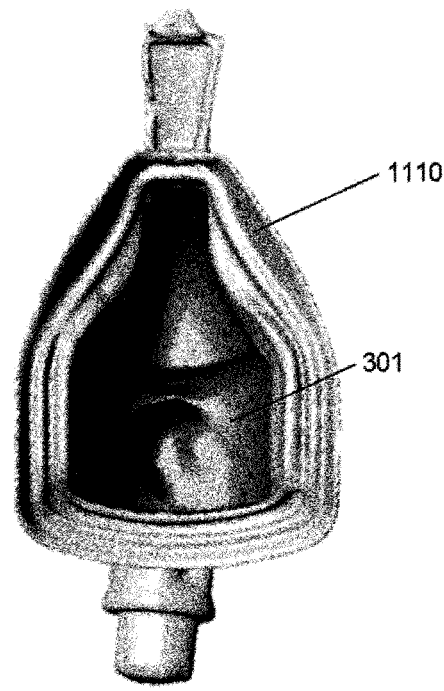
FIG. 11B is a back view of an exemplary mask incorporating the respiratory humidifying device.
Figure 11C:
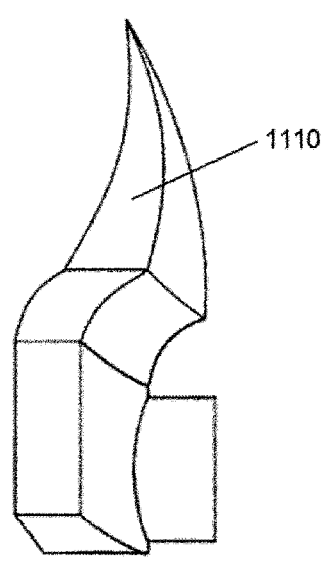
FIG. 11C is a side view of an exemplary mask incorporating the respiratory humidifying device.
Figure 11D:
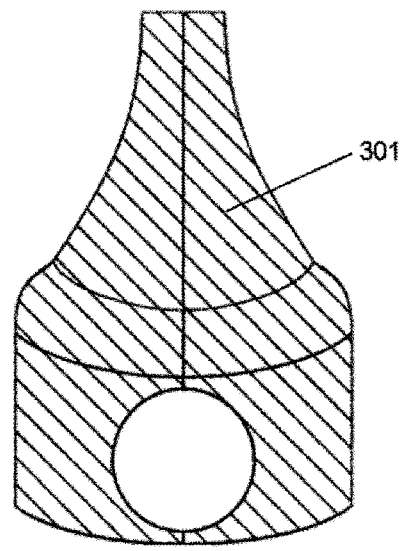
FIG. 11D is a partial back view of an exemplary mask incorporating the respiratory humidifying device.

The air flow of a patient using the respiratory humidifying device 301 is illustrated in FIG. 10. The patient 1010 breaths in and out 1020 through a mask 1050 having the fibrous cotton 330 with a resistor filament 340 sewn in. During expiration, the hydrophilic properties 1040 of the mask 1050 extracts moisture from the air expelling dry air 1031. During inhalation, the mask is heated 1055 using the filament 340 so the mask 1050 has hydrophobic properties. Fresh air 1030 passes through the mask and moisture is added to the incoming air such that humid air is provided to the patient 1010.

Figure 18:
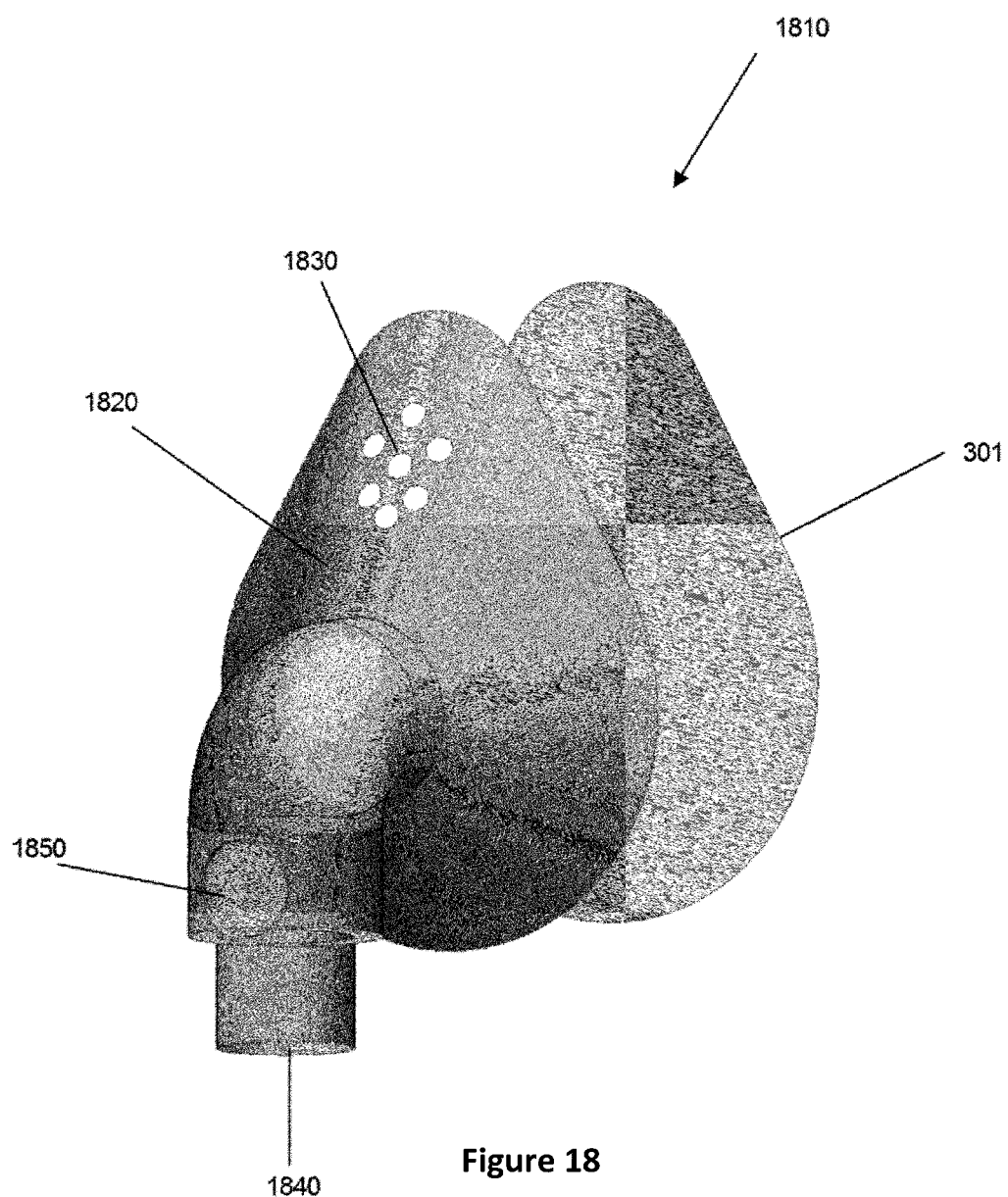
FIG. 18 is a view of a further exemplary mask incorporating the respiratory humidifying device.
Figure 19A:
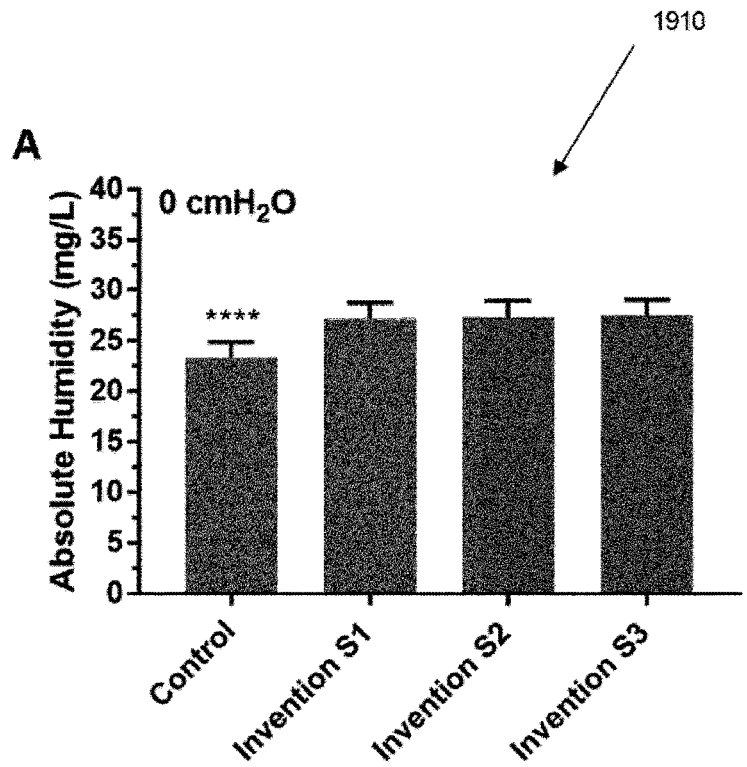
FIGS. 19A/B-23A/B are graphs of the results of the results of trials using an exemplary respiratory humidifying device.
Figure 19B:
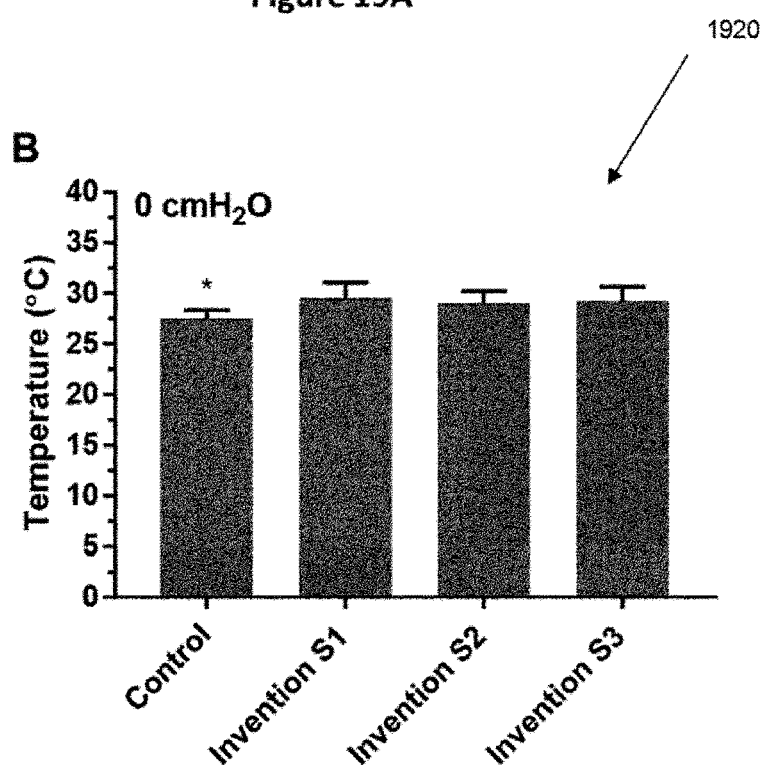

A further exemplary facemask 1810 can be seen in FIG. 18 including the respiratory humidifying device 301 (composed by the PNIPAM-cotton material 330 and the resistor filament 340), the mask 1720 including outflows 1830, 1850 and an inflow 1840 suitable for pressurised inflow.

Clinical Trials

The applicant conducted trials in order to test the humidity performance of the respiratory humidifying device 301 (composed by the PNIPAM-cotton material 330 and the resistor filament 340), three linear and medium molecular weight (between 7 and 20 kDa) PNIPAM-cotton samples were synthetized (S1, S2, and S3). Then, the samples were sewed with the insulated copper filament, the ends were weld to the male copper snaps and sewed to the fabric with a cotton thread to ensure its fixation.

Female copper snaps were glued to a CPAP mask and welded to copper wires. Both wires were connected to a power supply (EL155R) (TTi) to provide the desired current and voltage to the filament. A SRD-05VDC-SL-C relay (Songle®) was connected between the power supply and one of the female copper snaps attached to the mask in order to switch the power on and off. The relay was connected to a UNO Arduino board and a computer. A SHT15 temperature and humidity sensor (Sensirion AG, Switzerland) was placed inside the CPAP mask and connected to the same UNO Arduino board. Code was written using the Arduino v1.6.11 software to set the relay switch on and off times and to collect the environmental temperature (T) and relative humidity (RH) data provided by the SHT15 sensor. A commercial CPAP device (FP Healthcare, NZ) was used to provide the positive airway pressure in the respiratory tract.

Figure 17:
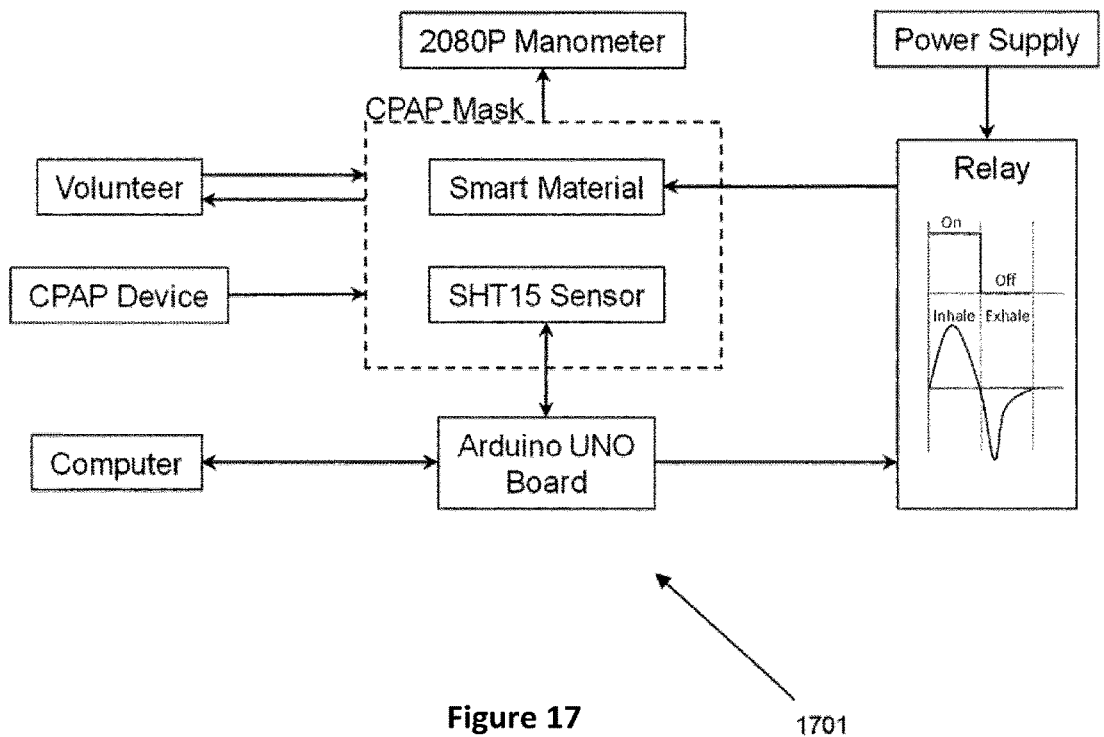
FIG. 17 is a diagram showing an example trial setup for testing and embodiment.

0, 5, 10, 15 and 20 cmH2O pressures were used in the trials, and a 2080P digital manometer (Digitron, UK) was connected to the mask to ensure that the respiratory humidifying device 301 (composed by the PNIPAM-cotton material 330 and the resistor filament 340) was not increasing the flowrate resistance and the pressure reading corresponds to the set on the CPAP device. Volunteer wear the CPAP mask to provide the breathing cycle which is tested during the trials. This experimental setup is outlined 1701 in FIG. 17.

Data Validation

To test the humidifying performance of the respiratory humidifying device 301, for each volunteer, the RH and T evolution inside the mask were measured with the SHT15 sensor. Then, the absolute humidity (AH) was calculated in order to compare the data obtained from each volunteer at each pressure applied from the CPAP device (0, 5, 10, 15 and 20 $cmH_2O$).

A control measurement was achieved using the CPAP device at each pressure i.e. the volunteer was breathing with the CPAP mask connected to the CPAP device, but without the respiratory humidifying device 301. This setup allowed for the measurement of absolute humidity provided by the fabric compared to a no humidified CPAP performance.

A third scenario was considered to validate the humidity provided by the respiratory humidifying device 301 at each pressure. Each volunteer tested breathing with the CPAP mask, without the fabric, connected to the CPAP device and with the CPAP humidifier working to provide the maximum humidity to the respiratory system. This setup allowed for the comparison of the humidity provided by the respiratory humidifying device 301 with the humidity provided by a commercial CPAP Clinical Protocol All the materials were washed and sterilized with 70% ethanol (Sigma Aldrich, NZ) before each test. The methodology followed with each volunteer is described below:

The volunteer was invited to wear the CPAP mask without the respiratory humidifying device 301 with the mask disconnected from the CPAP device and breathe for 5 minutes. The RH and T data was used to analyse the shape of the breathing cycle and determine the how long took the inspiration and expiration phases. Then, the relay was adjusted to switch on the power during inspiration and switch it off during expiration. The data was also used to quantify the natural humidity evolution without any extra humidification at 0 $cmH_2O$ pressure.

The respiratory humidifying device 301 was connected to the CPAP mask and the electrical resistance of the system was measured to calculate the current and voltage needed to achieve a maximum temperature of 42° C. Ohm's law and equation 1 were used to calculate the values.

The volunteer was invited to wear the CPAP mask containing the respiratory humidifying device 301 and disconnected from the CPAP device and breathe for 5 minutes. The E5 IR camera (FLIR) was used to measure the temperature evolution on the fabric surface and ensure the minimum and maximum temperatures were around 26° C. and 42° C. respectively. The T and RH readings were used to determine the humidity provided by the respiratory humidifying device 301 at 0 $cmH_2O$ pressure.

Then, the CPAP device was set to provide 5 $cmH_2O$ positive pressure and was connected to the mask. The volunteer was invited to wear the CPAP mask without the respiratory humidifying device 301 and breathe for 5 minutes. Then, the volunteer was invited to wear the CPAP mask with the respiratory humidifying device 301 and breathe for 5 minutes. Finally, the volunteer was invited to wear the CPAP mask without the respiratory humidifying device 301 but with the CPAP humidifier working at maximum humidification and breathe for 5 minutes. The temperature on the fabric surface was measured multiple times with the E5 IR camera to adjust the current and voltage provided and ensure the minimum and maximum temperatures were around 26° C. and 42° C. respectively. The maximum current and voltage provided to the copper resistor filament were 1.5 A and 5.28 V respectively.

The last step was repeated with 10, 15 and 20 cmH2O positive airway pressures and the T and RH data was collected and stored for analysis.

Results

The results obtained from the clinical trials show the AH and T values measured inside the CPAP mask in the volunteers. The data shown corresponds to the median of the signal obtained from the volunteers under each scenario: 1) control, where no humidity is provided, 2) heat and humidity provided from the respiratory humidifying device 301 (three equally-synthetized samples are tested: S1, S2 and S3) and 3) humidity provided by the commercial CPAP humidifier at the maximum level.

Under 0 cmH2O, where the CPAP device is not used, the humidity and temperature provided from the three samples are significantly higher than the control. No significant differences are found between the three samples which proves repeatability of the results.

Figure 20A:
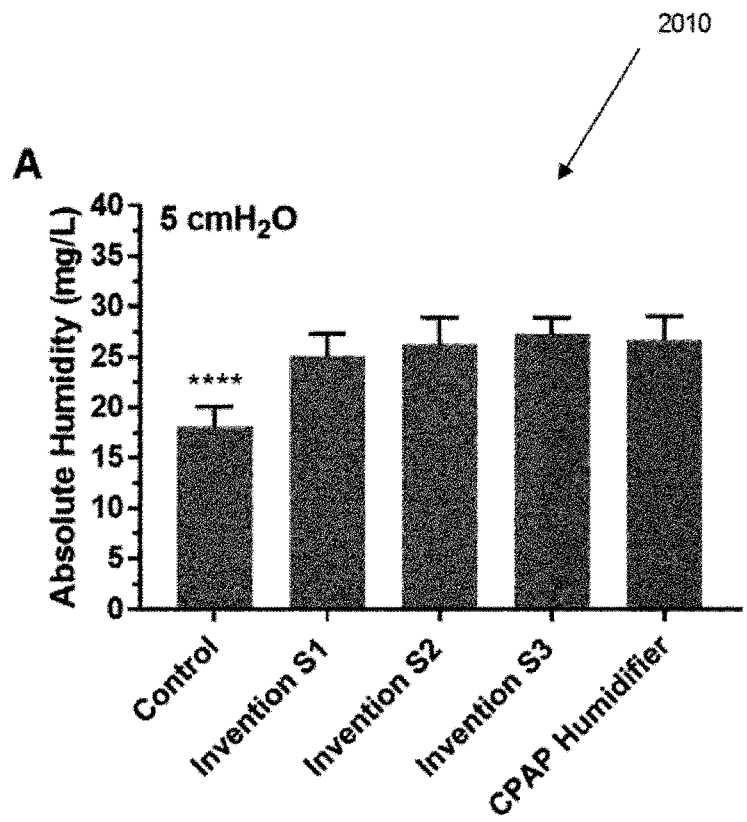
Figure 20B:
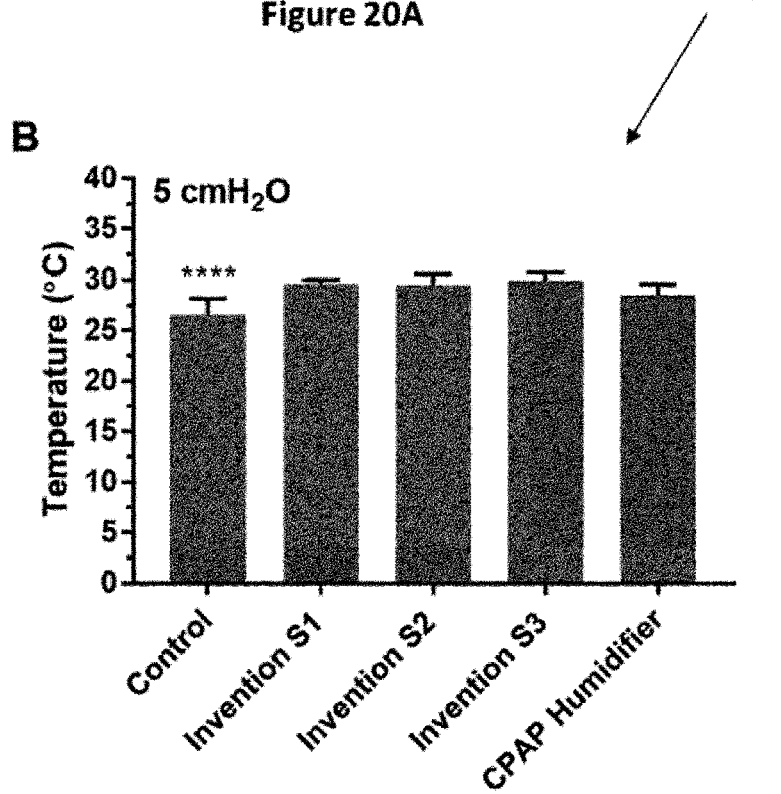

FIGS. 20A and 20B 2010 and 2020 show the clinical data obtained from the volunteers at 0 $cmH_2O$ (no CPAP used). FIG. 20A 2010 shows the absolute humidity inside the CPAP mask obtained from the control and the three sample S1, S2 and S3. FIG. 20B 2020 shows the environmental temperature inside the CPAP mask obtained from the control and the three samples S1, S2 and S3. The data shows a mean±standard deviation, n=21 (*$p<0.05$, $p<0.01$, *$p<0.001$ and ****$p<0.0001$).

Figure 21A:
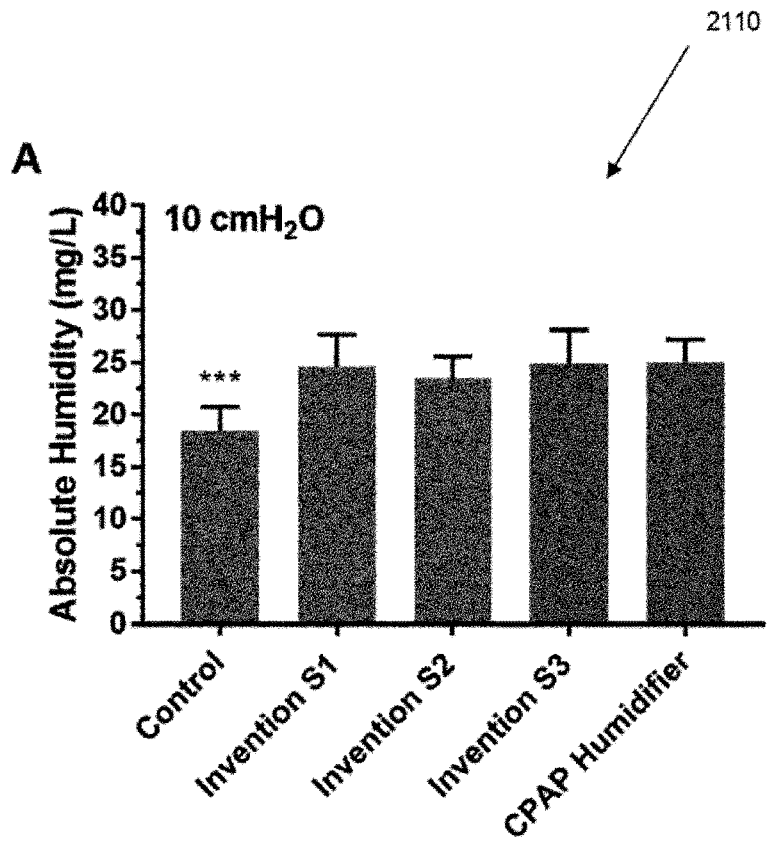
Figure 21B:
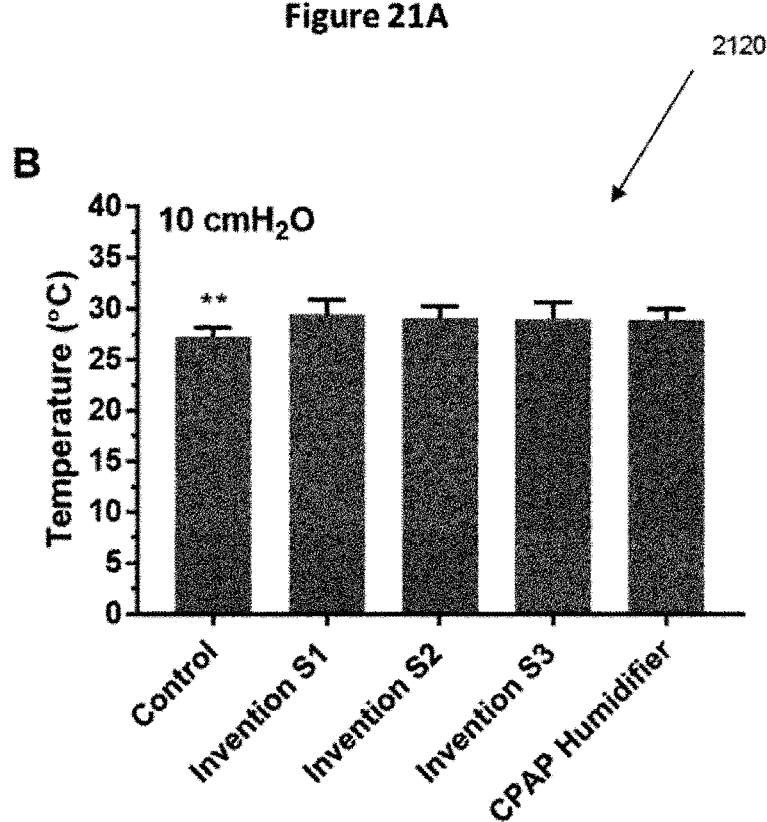

Under 5 $cmH_2O$, the humidity and temperature provided from the three samples is significantly higher than the control. No significant differences are found between the three samples which proves repeatability of the results. Also, no significant differences are found between the humidity and heat provided from any of the three samples and the commercial CPAP humidifier, which proves that the respiratory humidifying device 301 could replace the current humidifier FIGS. 21A and 21B 2110 and 2120 show the clinical data obtained from the volunteers at 5 $cmH_2O$ (CPAP device used). FIG. 21A 2110 shows the absolute humidity inside the CPAP mask obtained from the control and the three sample S1, S2 and S3. FIG. 21B 2120 shows the environmental temperature inside the CPAP mask obtained from the control and the three samples S1, S2 and S3. The data shows a mean±standard deviation, n=21 (*$p<0.05$, $p<0.01$, *$p<0.001$ and ****$p<0.0001$).

Under 10 $cmH_2O$, the humidity and temperature provided from the three samples are significantly higher than the control. No significant differences are found between the three samples which proves repeatability of the results. Also, no significant differences are found between the humidity and heat provided from any of the three samples and the commercial CPAP humidifier, which proves that the respiratory humidifying device 301 could replace the current humidifier.

Figure 22A:
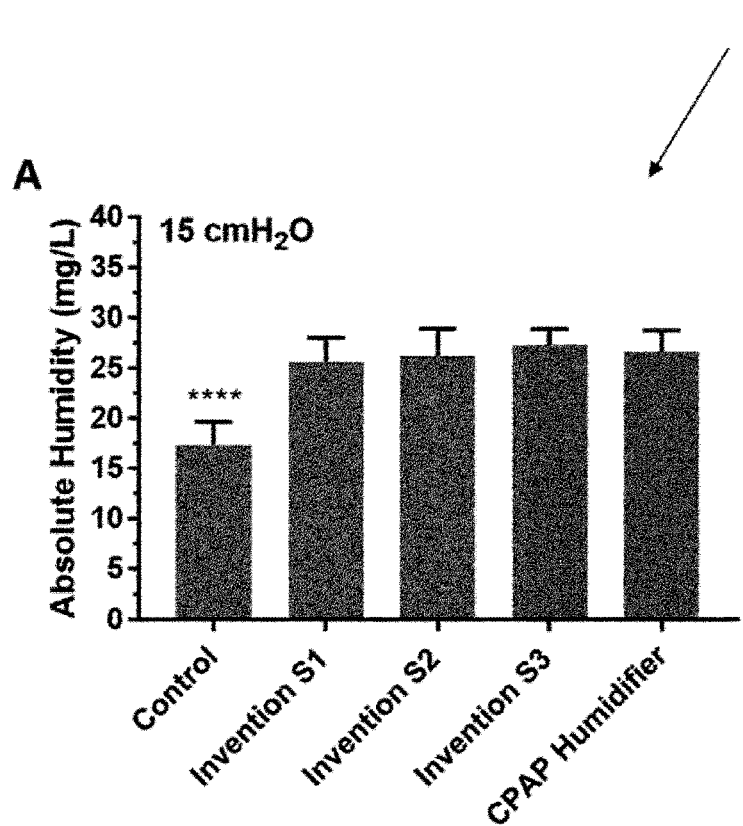
Figure 22B:
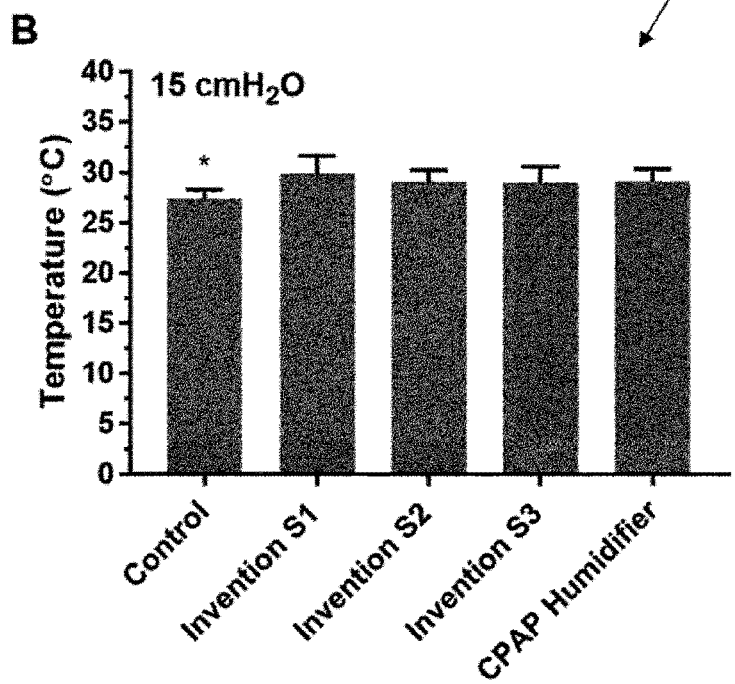

FIGS. 22A and 22B 2210 and 2220 show the clinical data obtained from the volunteers at 10 $cmH_2O$ (CPAP device used). FIG. 22A 2210 shows the absolute humidity inside the CPAP mask obtained from the control and the three sample S1, S2 and S3. FIG. 22B 2220 shows the environmental temperature inside the CPAP mask obtained from the control and the three samples S1, S2 and S3. The data shows mean±standard deviation, n=21 (*p<0.05, p<0.01, *p<0.001 and ****p<0.0001).

Under 15 cmH$_2$O, the humidity and temperature provided from the three samples are significantly higher than the control. No significant differences are found between the three samples which proves repeatability of the results. Also, no significant differences are found between the humidity and heat provided from any of the three samples and the commercial CPAP humidifier, which proves that the respiratory humidifying device 301 could replace the current humidifier.

Figure 23A:
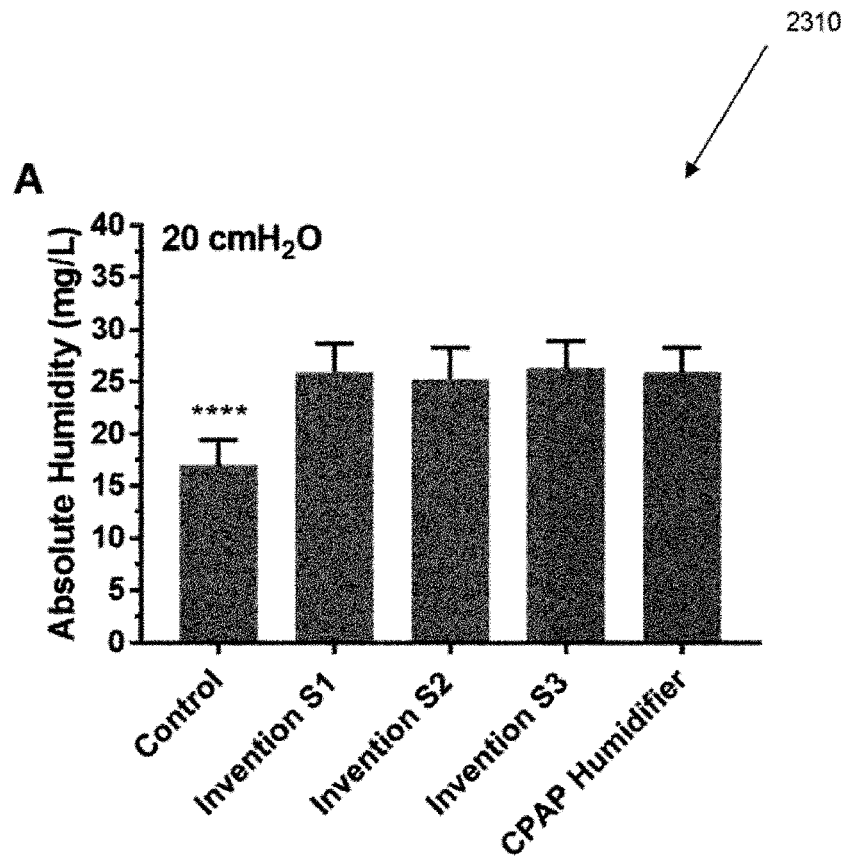
Figure 23B:
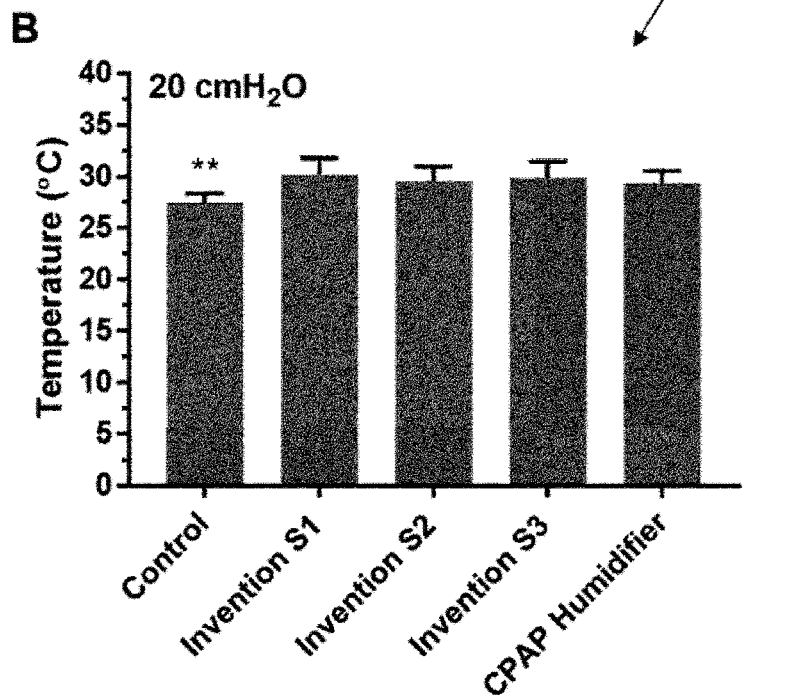

FIGS. 23A and 23B 2310 and 2320 show the clinical data obtained from the volunteers at 15 cmH$_2$O (CPAP device used). FIG. 23A 2310 shows the absolute humidity inside the CPAP mask obtained from the control and the three sample S1, S2 and S3. FIG. 23B 2320 shows the environmental temperature inside the CPAP mask obtained from the control and the three samples S1, S2 and S3. The data shows mean±standard deviation, n=21 (*p<0.05, p<0.01, *p<0.001 and ****p<0.0001).

Under 20 cmH$_2$O, the humidity and temperature provided from the three samples are significantly higher than the control. No significant differences are found between the three samples which proves repeatability of the results. Also, no significant differences are found between the humidity and heat provided from any of the three samples and the commercial CPAP humidifier, which proves that the respiratory humidifying device 301 could replace the current humidifier.

FIGS. 24A and 24B 2410 and 2420 show the clinical data obtained from the volunteers at 20 cmH$_2$O (CPAP device used). FIG. 23A 2310 shows the absolute humidity inside the CPAP mask obtained from the control and the three sample S1, S2 and S3. FIG. 23B 2320 shows the environmental temperature inside the CPAP mask obtained from the control and the three samples S1, S2 and S3. The data shows mean±standard deviation, n=21 (*p<0.05, p<0.01, *p<0.001 and ****p<0.0001.

The clinical results illustrate that no significant differences exist between the humidity and heat provided from any of the three samples and the commercial CPAP humidifier, which proves that the respiratory humidifying device 301 could replace the current humidifier.

While the present invention has been illustrated by the description of the embodiments thereof, and while the embodiments have been described in detail, it is not the intention of the Applicant to restrict or in any way limit the scope of the appended claims to such detail. Additional advantages and modifications will readily appear to those skilled in the art. Therefore, the invention in its broader aspects is not limited to the specific details, representative apparatus and method, and illustrative examples shown and described. Accordingly, departures may be made from such details without departure from the spirit or scope of the Applicant's general inventive concept.

The invention claimed is:

1. A respiratory humidifying apparatus comprising:
a moisture exchange fabric positioned so that a respiratory system inspiration and expiration airflow is in contact with the moisture exchange fabric, the moisture exchange fabric comprising:
   a substrate fabric, and
   a temperature-responsive polymer having lower critical solution temperature (LCST) of between 25° C. and 39° C. bonded to the substrate fabric;
a heater for heating the moisture exchange fabric;
a power supply for supplying power to the heater; and
a controller controlling the supply of power to the heater such that during inspiration when the moisture exchange fabric is heated and moisture is added to the incoming air such that humid air is provided to a user and during expiration the moisture exchange fabric extracts moisture from the air.

2. The respiratory humidifying apparatus of claim 1 wherein the moisture exchange fabric is not heated during expiration.

3. The respiratory humidifying apparatus of claim 1 wherein the controller switches the power on and off according to typical inspiration and expiration phases.

4. The respiratory humidifying apparatus of claim 1 wherein the controller controls the supply of power to the heater based on the information from at least one sensor such that the power is on during inspiration and off during expiration.

5. The respiratory humidifying apparatus of claim 4 wherein the controller controls the supply of power to the heater based on the information from the at least one sensor such that the power is off during expiration.

6. The respiratory humidifying apparatus of claim 1 where during inspiration the power supply is on in order to overcome the LCST temperature and to allow the moisture exchange fabric to release water molecules previously absorbed.

7. The respiratory humidifying apparatus of claim 1 wherein the controller controls the percentage of water released as a function of the temperature based on a temperature calibration curve.

8. The respiratory humidifying apparatus of claim 1 wherein the substrate fabric is a hydrophilic fabric.

9. The respiratory humidifying apparatus of claim 1 wherein the substrate fabric is selected from the group consisting of natural fibres and processed fibres.

10. The respiratory humidifying apparatus of claim 1 wherein the substrate fabric is selected from the group consisting of cotton, linen, chitin, chitosan, rayon, polyvinyl alcohol (PVA), and polypropylene.

11. The respiratory humidifying apparatus of claim 1 wherein the polymer is PNIPAM.

12. The respiratory humidifying apparatus of claim 1 wherein the polymer is selected from the group consisting of Elastin-like oligo- and polypeptides, Poly(acrylic acid-co-acrylamide), Poly(methyl vinyl ether) (PMVE), Poly(oxazoline)s, Poly(N-vinyl caprolactam) (PVC), and Poly(N-alkylacrylamide)s.

13. The respiratory humidifying apparatus of claim 1 further including a mask adapted to encompass a user's nose and/or mouth, the mask having at least one air passage adapted to permit air to enter and leave the mask, and wherein the moisture exchange fabric is positioned so that the respiratory system inspiration and expiration airflow is in contact with the moisture exchange fabric.

14. The respiratory humidifying apparatus of claim 1 wherein the apparatus is used for CPAP therapy.

15. A self-humidified mask comprising the respiratory humidifying apparatus of claim 1.

16. A method of controlling the water vapour release and absorption of a moisture exchange fabric providing humidified air to a user positioned so that a respiratory system inspiration and expiration airflow is in contact with the moisture exchange fabric, the moisture exchange fabric comprising a substrate fabric and a temperature responsive polymer having a lower critical solution temperature (LCST) of between 25° C. and 39° C. bonded to the substrate fabric, the method comprising using a controller to control a heater by controlling the supply of power to the heater such that during inspiration the moisture exchange fabric is heated and moisture is added to incoming air such that humid air is provided to a user and during expiration the moisture exchange fabric extracts moisture from the air.

17. The method of claim 16 wherein the moisture exchange fabric is heated to overcome the lower critical solution temperature (LCST) of the moisture exchange fabric.

18. The method of claim 16 further comprising controlling the supply of power to the heater such that during expiration the moisture exchange fabric is not heated and the moisture exchange fabric extracts moisture from the air.

19. The method of claim 16 further comprising:
identifying the temperature required for the fabric to release the required amount of water vapour from a calibration curve; and
controlling the heater to adjust the temperature of the moisture exchange fabric to release the required amount of water vapour.

20. The method of controlling the water vapour release and absorption of a moisture exchange fabric as claimed in claim 16 wherein the controller controls the heater by controlling a power supply and wherein the controller controls the voltage and current of the power supply.

* * * * *